US006242623B1

(12) United States Patent
Boussie et al.

(10) Patent No.: US 6,242,623 B1
(45) Date of Patent: Jun. 5, 2001

(54) COMPOSITIONS AND METAL COMPLEXES HAVING ANCILLARY LIGANDS

(75) Inventors: Thomas Boussie, Menlo Park; Vince Murphy, Cupertino; Johannes A. M. van Beek, Mountain View, all of CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/119,318

(22) Filed: Jul. 20, 1998

Related U.S. Application Data

(63) Continuation-in-part of application No. 08/898,715, filed on Jul. 22, 1997, now Pat. No. 6,030,917.
(60) Provisional application No. 60/077,808, filed on Mar. 12, 1998.

(51) Int. Cl.[7] .............................. C07F 9/00; C07F 17/00; C08F 4/44; B01J 31/00
(52) U.S. Cl. ................................ 556/18; 556/19; 556/57; 556/146; 556/150; 526/160; 526/943; 502/104; 502/150
(58) Field of Search .................................. 556/18, 19, 57, 556/146, 150; 502/104, 150; 526/160, 943

(56) References Cited

PUBLICATIONS

Fernandez, Eduardo, J., et al., "Strong Activation of the Double Bond in $(PPh_2)_2C:CH_2$. Novel Synthesis of Gold(III) Methanide Complexes by Michael Addition Reactions," *Chemical Abstracts*, vol. 126, No. 15, abstract No. 199625, (Apr. 14, 1997).

Hursthouse, Michael, B., et al., "Synthesis and X–Ray Crystal Structures of the Homoleptic Tris(1,3–Diphenylacetamidinato) Complexes $M/Ph=NC(Me) NPh/_3$] (M=Ruthenium, Rh), the Rhodium(III) Triazenido Analog $[Rh(PhNNNPh)_3]$ and the Corresponding Rhodium(II) Derivative $[Rh_3(PhNNNPh)_4]$," *Chemical Abstracts*, vol. 119, No. 2, abstract No. 19279, (Jul. 12, 1993).

Abd–Ellah, I.M., et al., "Synthesis and Characterization of Some New Complexes of Phosphine Schiff Base Derivatives," *Chemical Abstracts*, vol. 113, No. 24, abstract No. 223346, (Dec. 10, 1990).

Clark, J. Andrew, et al., "Amidino–Complexes of Iron(II) and (III)," *Chemical Abstracts*, vol. 100, No. 24, abstract No. 202345, (Jun. 11, 1984).

Rigby, William, et al., "Pentamethylcyclopentadienyl–Rhodium and –Iridium Complexes. Part 21. Neutral and Cationic β–Diketonato–, $η^3$–Allylic, and NN" –Triazenido–Complexes: the X–Ray Crystal Structure of the Binuclear Complex $[Rh_2(C_5Me_5)_2(acac)_2] [BF_4]_2$, *J. Chem. Soc.*, vol. 2, pp. 387–394, (1979).

*Primary Examiner*—Porfirio Nazario-Gonzalez

(57) ABSTRACT

Novel compositions and metal compounds having an ancillary ligand structure polymerize monomers and functionalized monomers, either alone or in the presence of an activator. The ancillary ligand structure is a chelating ligand that may optionally be further bound to the metal via a dative or covalent bond.

24 Claims, No Drawings

COMPOSITIONS AND METAL COMPLEXES HAVING ANCILLARY LIGANDS

This application is a continuation-in-part of application Ser. No. 08/898,715, filed Jul. 22, 1997, now U.S. Pat. No. 6,030,917 and claims priority from provisional application Ser. No. 60/077,808, filed Mar. 12, 1998, with the teachings of both incorporated herein by reference for all purposes.

FIELD OF THE INVENTION

The present invention relates to compositions and metal complexes that are useful as catalysts and in particular olefin polymerization catalysts.

BACKGROUND OF THE INVENTION

Ancillary ligand stabilized metal complexes (e.g., organometallic complexes) are useful as catalysts, additives, stoichiometric reagents, monomers, solid state precursors, therapeutic reagents and drugs. The ancillary ligand system comprises organic substituents that bind to the metal center(s), remain associated with the metal center(s), and therefore provide an opportunity to modify the shape, electronic and chemical properties of the active metal center(s) of the organometallic complex.

Certain organometallic complexes are catalysts for reactions such as oxidation, reduction, hydrogenation, hydrosilylation, hydrocyanation, hydroformylation, polymerization, carbonylation, isomerization, metathesis, carbon-hydrogen activation, cross-coupling, Friedel-Crafts acylation and alkylation, hydration, dimerization, trimerization, oligomerization, Diels-Alder reactions and other transformations. Organometallic complexes can be prepared by combining an ancillary ligand precursor with a suitable metal precursor in a suitable solvent at a suitable temperature.

One example of the use of organometallic complexes is in the field of single-sited olefin polymerization catalysis. The active site typically comprises an ancillary ligand-stabilized, coordinatively unsaturated transition metal alkyl complex.

It is always a desire to discover new catalysts and catalyst systems that may catalyze reactions differently from known ligand systems. This invention provides new compositions, metal compounds and catalyst systems.

SUMMARY OF THE INVENTION

In one aspect, this invention relates to ancillary ligands that are combined with metal precursors to form an active catalyst composition. The ancillary ligands can be described by the general formula:

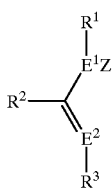

where $E^1$ and $E^2$ are elements, each of which is, independently, selected from the group consisting of N, P, O, S and Se;

Z is an element or molecule selected from the group consisting of H, Li, TMS, SnBu$_3$, Na, K, Rb, Ti, Ag and MgT, where T is a halogen (F, Cl, Br and I);

$R^1$ and $R^3$ are groups that may be independently selected from the group consisting of alkyl, substituted alkyl, aryl and substituted aryl;

$R^2$ is a group that may be selected from the group consisting of hydrocarbyl, alkoxides, aryloxides (—OX), thioethers, (—SX) phosphines (—PX$_2$), arsines (—AsX$_2$), silanes (—SiX$_3$), germanes (—GeX$_3$), amides (—NX$_2$) and combinations thereof. In each of these formulas, X is selected from the group consisting of alkyls, aryls, substituted alkyls and substituted aryls and combinations thereof.

In this first aspect, the ancillary ligand is combined with a metal precursor to form a composition. The metal precursors can be described by the general formula:

$$R'_a ML_b T_c$$

where M is a metal selected from Groups 2–12 of the Periodic Table of Elements;

R' is a group that forms a bond with M such that an olefin, diolefin or acetylenically unsaturated monomer or a functionalized version thereof (such as a functionalized olefin) can insert into the bond between R' and M. R' is typically selected from the group consisting of hydrocarbyl, silyl, germyl and hydride; a is 1, 2, 3 or 4 depending on the oxidation state of M.

L is an optional ligand, which, when present is a dative ligand (including agostic interactions), which can be selected from the group consisting of olefins, functionalized olefins, ethers, pyridines, nitriles, thioethers, phosphines, amines carbonyls and combinations thereof; and b is 0, 1, 2, 3 or 4.

T is a halogen and c is 0, 1 or 2. The halogen is present in certain embodiments.

In another aspect, this invention relates to compounds, which can be described by the general formula:

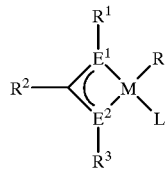

or a dimer, trimer or higher aggregate thereof, wherein M is a metal selected from Groups 7–12 of the Periodic Table of Elements;

$E^1$ and $E^2$ are elements, each of which is, independently, selected from the group consisting of N, P, O, S and Se;

R' is a group that forms a bond with M such that an olefin, diolefin or acetylenically unsaturated monomer or a functionalized version thereof (such as a functionalized olefin) can insert into the bond between R' and M. R' is typically selected from the group consisting of hydrocarbyl, silyl, germyl and hydride.

L is an optional ligand, which, when present is a dative ligand (including agostic interactions), which can be selected from the group consisting of olefins, functionalized olefins, ethers, pyridines, nitriles, thioethers, phosphines, amines, carbonyls and combinations thereof.

$R^1$ and $R^3$ are groups that may be independently selected from the group consisting of alkyl, substituted alkyl, aryl and substituted aryl;

$R^2$ is a group that may be selected from the group consisting of hydrocarbyl, alkoxides, aryloxides (—OX), thioethers, (—SX) phosphines (—PX$_2$), arsines (—AsX$_2$), silanes (—SiX$_3$), germanes (—GeX$_3$), amides (—NX$_2$) and combinations thereof. In each of these formulas, X is selected from the group consisting of alkyls, aryls, substituted alkyls and substituted aryls and combinations thereof.

Additionally $R^2$ may bind further to the metal via a dative bond from one of the above group of molecules or through a functionality, Q, which can be depicted by the general formula:

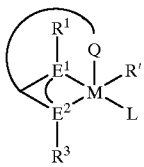

where Q is a functionality having a lone pair of electrons capable of dative binding to the metal. Generally, Q is a molecule including an atom selected from the group consisting of N, O, S, P and halogens (Cl, Br, I and F). When the functionality Q is present, M may be selected from the group consisting of Groups 2–12 of the Periodic Table of Elements. Also when Q is present, $R^2$ is generally a combination of the groups listed above, such that Q may be selected from the group consisting of heteroarylalkyls, substituted heteroarylalkyls, heterocyclicalkyls, substituted heterocyclicalkyls, alkylarines arylamines and the like.

Optionally, $R^2$ may further bind to the metal via two dative bonds from the group of molecules listed above or through the functionalities $Q^1$ and $Q^2$, where $Q^1$ and $Q^2$ may be the same or different, but each has the same definition as Q, above. This can be depicted by the general formula:

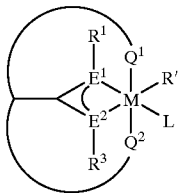

Alternatively, $R^2$ may bind further to the metal via a covalent bond such as depicted by the general formula:

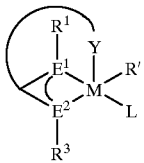

where Y is a functionality capable of covalently bonding to the metal. Generally Y is a molecule including an atom selected from the group consisting of N, O, S and P. Suitable groups are amides, phosphides, aryloxides, alkoxides, thiols and the like. When Y is present M may be selected from the group consisting of Groups 3–10 of the Periodic Table of Elements. Y is generally a combination of the groups listed above for $R^2$. For example, Y may be selected from the group consisting of heteroarylalkyls, substituted heteroarylalkyls, heterocyclicalkyls, substituted heterocyclicalkyls, alkylamines, arylamines and the like.

Additionally $R^2$ may bind further to the metal via two a covalent bonds from functionalities $Y^1$ and $Y^2$, where $Y^1$ and $Y^2$ may be the same or different, but each has the same definition as Y, above. Such a complex may be depicted by the general formula:

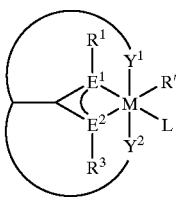

When both $Y^1$ and $Y^2$ are present, M may be selected from the group consisting of Groups 4–10 of the Periodic Table of Elements.

Optionally, $R^2$ may bind further to the metal via one covalent bond, and one dative bond such as depicted by the general formula:

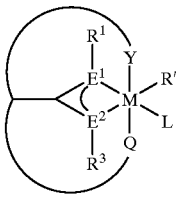

where Y and Q are as defined above and M can be selected from the group consisting of Groups 3–10 of the Periodic Table of Elements.

The complexes of this invention are suitable as catalysts for the polymerization of olefins. They may be used with or without an activator. Monomers that may be polymerized by the complexes of this invention are: olefins, diolefins and acetylenically unsaturated monomers, as well as functionalized versions thereof (such as a functionalized olefin).

DETAILED DESCRIPTION OF THE INVENTION

This invention relates to new compounds that polymerize olefins, diolefins and acetylenically unsaturated monomers. The compounds of this invention are also useful for polymerizing functionalized monomers without degradation of the functionalizing moiety. Examples of functionalized monomers useful with this invention are acrylates, acetates and arylonitriles. For further discussion of functionalized monomers, see PCT application published as WO 96/23010, herein incorporated by reference.

The phrases "characterized by the formula" or "represented by the formula" are used in the same way that "comprising" is commonly used. The term "independently selected" is used herein to indicate that the R groups, e.g., $R^1$, $R^2$, and $R^3$, can be identical or different (e.g. $R^1$, $R^2$ and $R^3$ may all be substituted alkyls or $R^1$ and $R^2$ may be a substituted alkyl and $R^3$ may be an aryl, etc.). A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "hydrocarbyl" is used herein to refer to a radical having only carbon and hydrogen atoms, including, e.g., alkyl and the like.

The term "alkyl" is used herein to refer to a branched or unbranched, saturated or unsaturated, monovalent hydrocarbon radical. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to alkyl as just described including one or more groups such as lower alkyl, aryl, acyl, halogen (i.e., alkylhalos, e.g., $CF_3$), hydroxy, amino, phosphido, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include substituted or unsubstituted phenyl, naphthyl, biphenyl, diphenylmethyl and benzophenone among others. In particular embodiments, aryls have between 1 and 200 carbon atoms, between 1 and 50 carbon atoms or between 1 and 20 carbon atoms.

"Substituted aryl" refers to aryl as just described including one or more groups such as lower alkyl, acyl, halogen, alkylhalos (e.g., $CF_3$), hydroxy, amino, phosphido, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone.

The term "acyl" is used to describe a ketone substituent, —C(O)J, where J is alkyl or substituted alkyl, aryl or substituted aryl as defined herein.

The term "amino" is used herein to refer to the group —NJJ', where J and J' may independently be hydrogen, alkyl, substituted alkyl, aryl, substituted aryl or acyl.

The term "alkoxy" is used herein to refer to the —OJ group, where J is an alkyl, substituted lower alkyl, aryl, substituted aryl, wherein the alkyl, substituted alkyl, aryl, and substituted aryl groups are as described herein. Suitable alkoxy radicals include, for example, methoxy, ethoxy, phenoxy, substituted phenoxy, benzyloxy, phenethyloxy, t-butoxy, etc.

As used herein, the term "phosphino" refers to the group —PJJ', where J and J' may independently be hydrogen, alkyl, substituted alkyl, aryl, substituted aryl or acyl.

As used herein, the term "mercapto" defines moieties of the general structure J—S—J' wherein J and J' are the same or different and are alkyl, aryl or heterocyclic as described herein.

The term "saturated cyclic hydrocarbon" denotes groups such as cyclopropyl, cyclobutyl, cyclopentyl, etc. and substituted analogues of these structures.

The term "unsaturated cyclic hydrocarbon" is used to describe a monovalent nonaromatic group with at least one double bond, such as cyclopentene, cyclohexene, etc. and substituted analogues thereof.

The term "heteroaryl" as used herein refers to aromatic rings in which one or more carbon atoms of the aromatic ring(s) are substituted by a heteroatom such as nitrogen, oxygen or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "alkyl" wherein the heteroaryl group is attached through an alkyl group as defined herein. For example, if $R^2$ is a heteroarylalkyl, the alkyl portion will be bonded to the carbon atom from which $R^2$ emanates and the heteroaryl portion will be a "substituent" on the alkyl that may datively bond to M (e.g., as a Q functionality).

"Substituted heteroaryl" refers to heteroaryl as just described wherein the heteroaryl nucleus is substituted with one or more groups such as alkyl, acyl, halogen, alkylhalos (e.g., $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted alkyls" as described above in which an alkyl group, as defined herein, links the heteroaryl group to the bonding point on the ligand.

The term "heterocyclic" is used herein to describe a monovalent saturated or unsaturated nonaromatic group having a single ring or multiple condensed rings from 1–12 carbon atoms and from 14 heteroatoms selected from nitrogen, phosphorous sulfur or oxygen within the ring. Such heterocycles are, for example, tetrahydrofuran, morpholine, piperidine, pyrrolidine, etc.

The term "substituted heterocyclic" as used herein describes a subset of "heterocyclics" wherein the heterocycle nucleus is substituted with one or more functional groups such as alkyl, acyl, halogen, alkylhalos (e.g., $CF_3$), hydroxy, amino, alkoxy, alkylamino, acylamino, acyloxy, mercapto, etc.

The term "heterocyclicalkyl" defines a subset of "alkyls" wherein an alkyl group, as defined herein, links the heterocyclic group to the bonding point on the molecule.

The term "substituted heterocyclicalkyl" defines a subset of "heterocyclic alkyl" wherein the heterocyclic nucleus is substituted with one or more groups such as alkyl, acyl, halogen, alkylhalos (e.g., $CF_3$), hydroxy, amino, alkoxy, alkylamino, acylamino, acyloxy, mercapto, etc.

Additionally, abbreviations used herein include:

Substituent X may occupy a single or multiple positions around the ring

Substituents X and Y may occupy single or multiple positions around the ring
(Ps) crosslinked polystyrene
Also, Ph=C$_6$H$_5$, Me=methyl, Et=ethyl, Pi=isopropyl, TMS=trimethylsilyl, Mes=2,4,6Me$_3$C$_6$H$_2$, Fc=ferrocene, Bu'=tertiary butyl, DMAT=o-dimethylaminotoluene, and DME=dimethoxyethane.

In one aspect, the compounds of this invention are metal compounds, which can be characterized by the general formula:

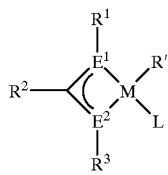

or a dimer or trimer or higher aggregate thereof,
wherein M is a metal selected from the group consisting of Groups 7–12 of the Periodic Table of Elements. More specifically, M is selected from the group consisting of Ni, Pd, Pt, Co, Fe, Mn, Cu and Zn.

R' is a group that allows an olefin, diolefin or acetylenically unsaturated monomer or a functionalized version thereof (such as a functionalized olefin) to insert into the bond between R' and M. R' is typically selected from the group consisting of hydrocarbyl, silyl, germyl, hydride and combinations thereof. R' will typically have less than 50 non-hydrogen atoms and preferably less than 20 non-hydrogen atoms. Specific examples of R' include methyl, ethyl, propyl, isopropyl, butyl, benzyl, phenyl, cyclopentadienyl, cyclohexyl, butadieneyl, pentadieneyl, trimethylsilyl, trimethylgermyl, triethylsilyl (trimethylsilyl)methyl, bis(trimethylsilyl)methyl, tris(trimethylsilyl)methyl and pentafluorophenyl.

L is optional, which when present is a dative ligand that shares electrons with M, but does not require a lone pair of electrons (e.g., including agostic interactions). L is selected from the group consisting of acetylenes, olefins, functionalized olefins, ethers, pyridines, nitriles, thioethers, phosphines, amines, carbonyls and combinations thereof. Specific examples of L include ethylene, propylene, dimethylether, methylethylether, acetonitrile, benzonitrile, pentafluorobenzonitrile, p-trifluoromethylbenzonitrile, 3,5-bis(trifluoromethyl)benzonitrile, tetrahydrofuran, trimethylphosphine, triphenylphosphine, dimethylphenylamine, pyridine, lutidine, and 4-Bu'-pyridine.

R$^1$ and R$^3$ are groups that may be independently selected from the group consisting of alkyl, substituted alkyl, aryl and substituted aryl. R$^1$ and R$^3$ typically have less than 50 non-hydrogen atoms and preferably less than 20 non-hydrogen atoms. Specific examples of R$^1$ and R$^3$ include methyl, ethyl, propyl, butyl, pentyl, hexyl, etc. (including primary, secondary and tertiary versions thereof), phenyl and 2,4,6-trimethylphenyl. Additionally, precursors to R$^1$ and R$^3$ are listed in Table 2, below.

R$^2$ is a group that may be selected from the group consisting of alkyls, substituted alkyls, aryls, substituted aryls, hydride, alkoxides, aryloxides (—OX), thioethers, (—SX) phosphines (-PX$_2$), arsines (—AsX$_2$), silanes (—SiX$_3$), germanes (—GeX$_3$), amides (—NX$_2$), heteroaryls, heteroarylakyls, substituted heteroaryls, substituted heteroarylalkyls, heterocyclics, substituted heterocyclics heterocyclicalkyls, substituted heterocyclicalkyls and combinations thereof. In each of these formulas, X is selected from the group consisting of alkyls, aryls, substituted alkyls and substituted aryls and combinations thereof. Specific examples of R$^2$ are hydride, methyl, ethyl, propyl, n-butyl, s-butyl, t-butyl, trimethylsilyl, phenyl, 3,5—(CF$_3$)$_2$C$_6$H$_3$-, phenol, thiophenol, ButO—, (CF$_3$)$_3$CO—, Me$_2$N—, (C$_6$H$_5$)$_2$N—, and (C$_6$H$_5$)$_2$P—, MeO—, PrO—, MeS— and 2,4,6—(CH$_3$)$_3$—$_6$H$_2$NH—. Additionally, precursors to R$^2$ are listed in Table 1, below.

Optionally R$^2$ may bind further to the metal via a dative bond from one of the above group of molecules or through a functionality and may be represented by Q, resulting in a complex which can be depicted by the general formula:

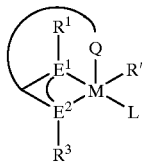

where Q is a functionality having a lone pair of electrons capable of dative binding to the metal. In this embodiment, M may be selected from the group consisting of Groups 2–12 of the Periodic Table of Elements. Generally, Q is a molecule including an atom selected from the group consisting of N, O, S and P. Q is generally a combination of the groups listed above for R$^2$. Q may be selected from the group consisting of heteroarylalkyls, substituted heteroarylalkyls, heterocyclicalkyls, substituted heterocyclicalkyls, alkylamines and the like. When the complexes of this invention take this form, specific examples of Q include

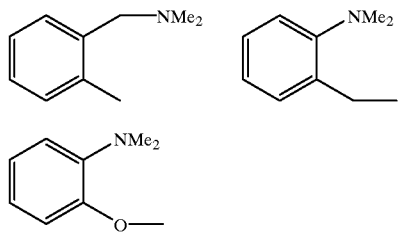

Depending on the specific molecules chosen for R$^2$, there may be two atoms that datively bind to the metal M, such that the complexes of this invention take the following form:

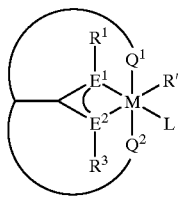

Here Q$^1$ and Q$^2$ have the same definition as Q and M may be selected from the group consisting of Groups 2–12 of the Periodic Table of Elements. Specific examples of $Q^1$ and $Q^2$ include

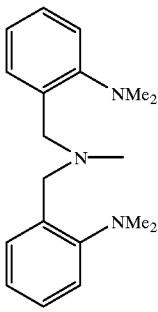 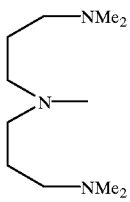

In other embodiments, the molecules chosen for $R^2$ may optionally include Y, which is a functionality capable of covalently bonding to the metal. Generally Y is a molecule including an atom selected from the group consisting of N, O, S and P. Suitable groups for Y are amides, phosphides, aryloxides, alkoxides, thiols and the like. When Y is present M may be selected from the group consisting of Groups 3–10 of the Periodic Table of Elements. Y is generally a combination of the groups listed above for $R^2$. For example, Y may be selected from the group consisting of heteroarylalkyls, substituted heteroarylalkyls, heterocyclicalkyls, substituted heterocyclicalkyls, alkylamines, arylamines and the like.

When Y is present, the complexes of this invention take the following form,

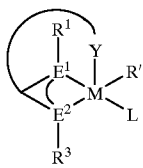

Specific examples of Y include

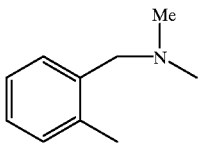 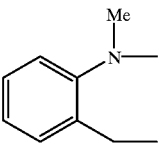

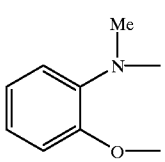

Alternatively, the complexes of this invention allow for $R^2$ to include two covalent bonds back to the metal, using $Y^1$ and $Y^2$ where the complexes of this invention take the following form:

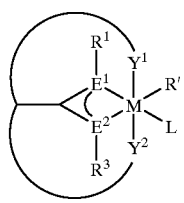

$Y^1$ and $Y^2$ have the same definition as Y. When both $Y^1$ and $Y^2$ are present, M may be selected from the group consisting of Groups 4–10 of the Periodic Table of Elements. Specific examples of $Y^1$ and $Y^2$ together include:

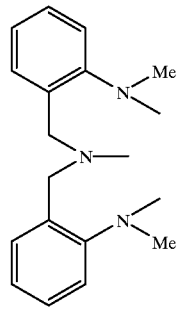 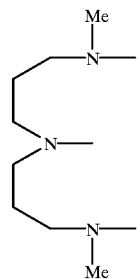

Alternatively, $R^2$ may be a group that further binds to the metal M via a dative bond and a covalent bond, such that the complexes of this invention take the following form:

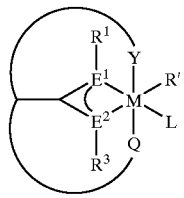

Y and Q have the same definitions as above. Specific examples of Q and Y together are:

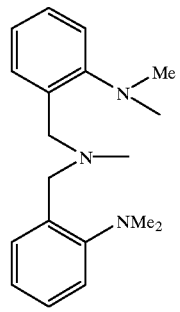 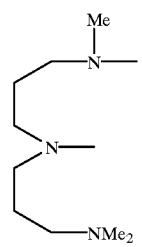

When Y and Q is present, M may be selected from the group consisting of Groups 3–10 of the Periodic Table of Elements.

As noted above, an alternative aspect of this invention is where two or more ancillary ligands and two or more metal precursors combine to form dimers, trimers or a higher aggregate of any one of the metal compounds discussed above. In this aspect, the metal compounds of this invention may take a form that can be characterized by the formula:

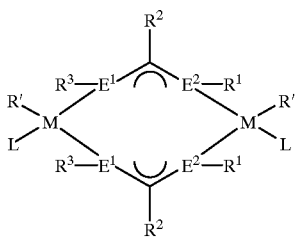

or an isomer thereof.

As also noted above, it is another optional aspect of this invention that multiple ancillary ligands combine with a single metal precursor. In this aspect, the metal complexes that are formed may be characterized by the general formula:

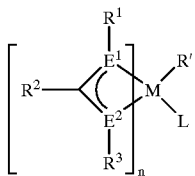

where n is 1, 2 or 3. Generally, n will depend on the metal chosen. Alternatively, this formulation could have more than one ancillary ligand and no R' or L; for example, n may be 2 and L and R' are not in the complex. In this alternative, activation to provide a bond for insertion is required for polymerization in the traditional Zielger-Natta mechanism.

It should be noted that in each of the above formulas for a metal compound (or metal complex), it is intended that the same definition of $R^1$, $R^2$, $R^3$, $E^1$, $E^2$, L, Y, $Y^1$, $Y^2$, Q, $Q^1$, $Q^2$, J, J' and X applies to each formula. The definition of M changes, as noted above, depending of the exact metal compound formula. Moreover, it should be understood that within the above stated limits for M, M may be any metal in Groups 2, 3, 4, 5, 6, 7, 8, 9, 10, 11 or 12 and is not limited simply because a range is listed for M. Also, the definition of R' may change as discussed below.

Exemplary compounds of this invention include:

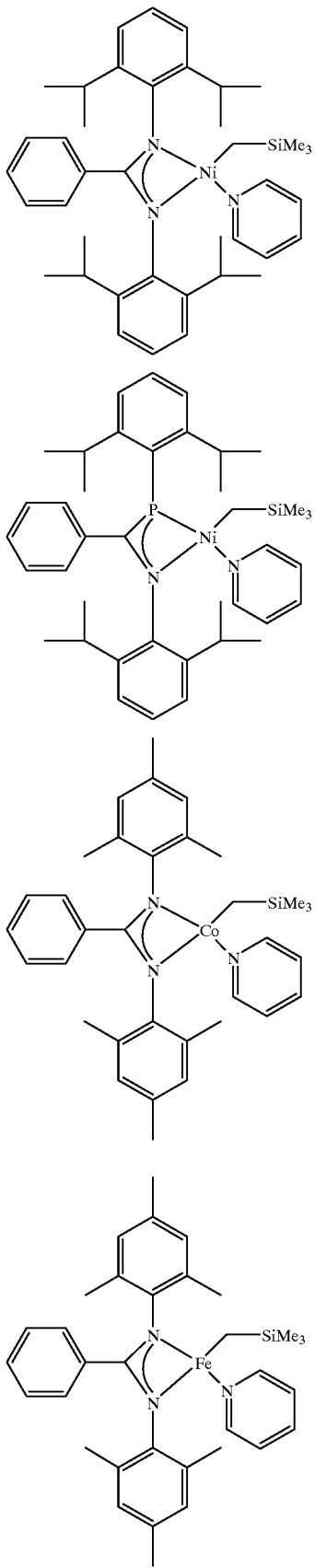

-continued
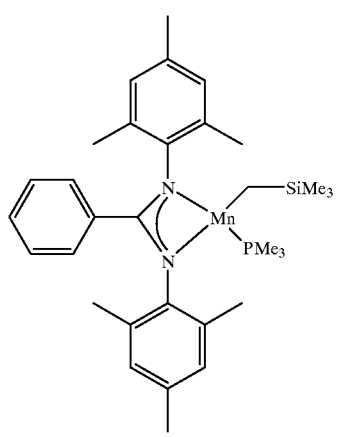
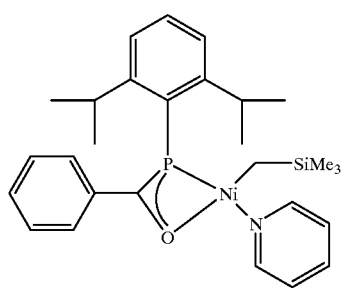
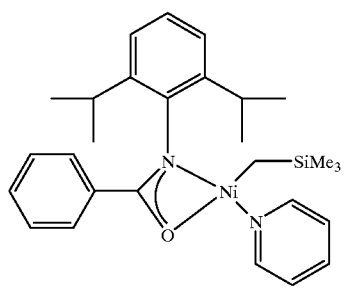
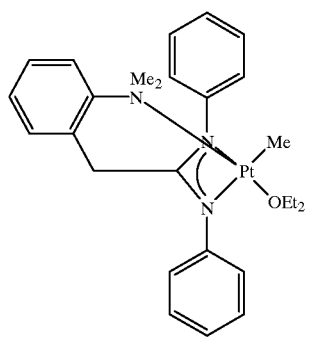
-continued
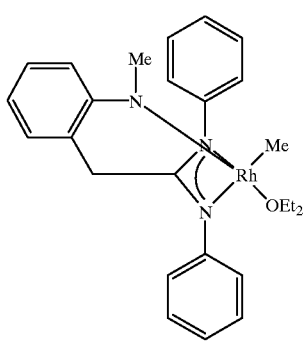
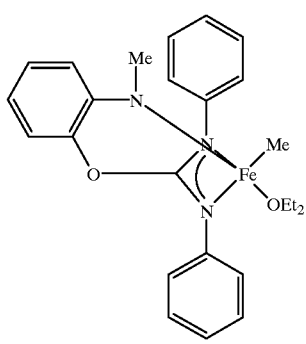
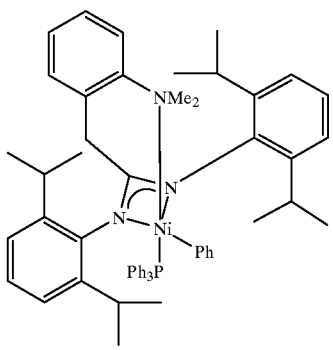
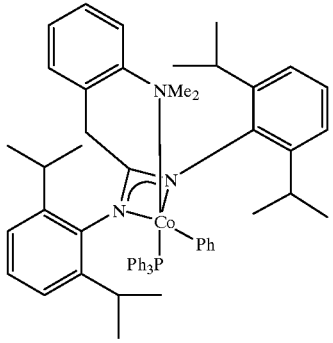

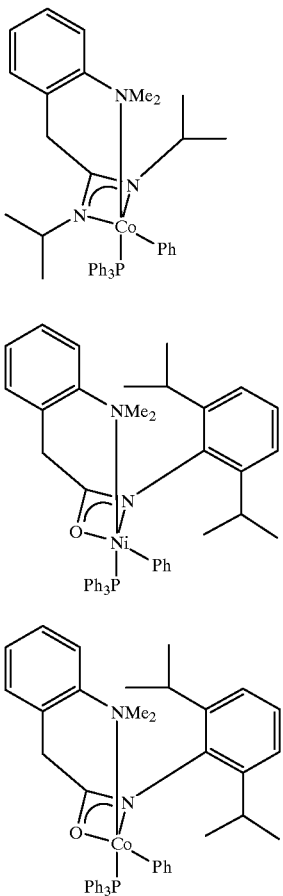

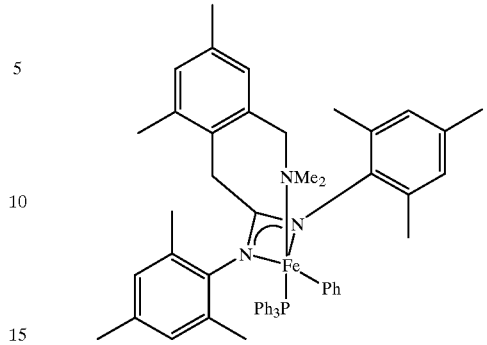

In an alternative embodiment, R' can be a halogen (such as Cl, Br, F or I), an amide (such as dimethylamino), an alkoxide or aryloxide or a thiol. In this embodiment, the complexes of this invention are not generally considered active catalysts in the traditional Zielger-Natta or Kaminsky-Sinn mechanism until the R' halogen group has been replaced with a group that generally allows a monomer to insert into the bond between M and R'. Such substitution can take place by the addition of certain activators (such as alumoxanes, especially methylalumoxane) which will replace these R' group in situ. Such substitution can also take place via other reactions known in the art, such a ligand substitutions reactions. For example, if the R' halogen ligand is Cl, then reaction with methyllithium (MeLi) will generally substitute a methyl group for the chlorine group. The conditions for this and other ligand substitution reactions are well known. See, for example, Comprehensive Organometallic Chemistry II Volumes I–XIV 1995. Pergamon Press. Editors: Abel, Stone and Wilkinson.

Generally, the compounds of this invention are prepared by forming the ancillary ligand and then attaching the metal to the ligand by the addition of a metal precursor. For example, certain ancillary ligands useful in this invention are made from an isocyanate, or by combining a isocyanate and an amine to form the carbodiimide, and then functionalizing the central carbon atom, all of which can be shown by the following Scheme 1:

Scheme 1

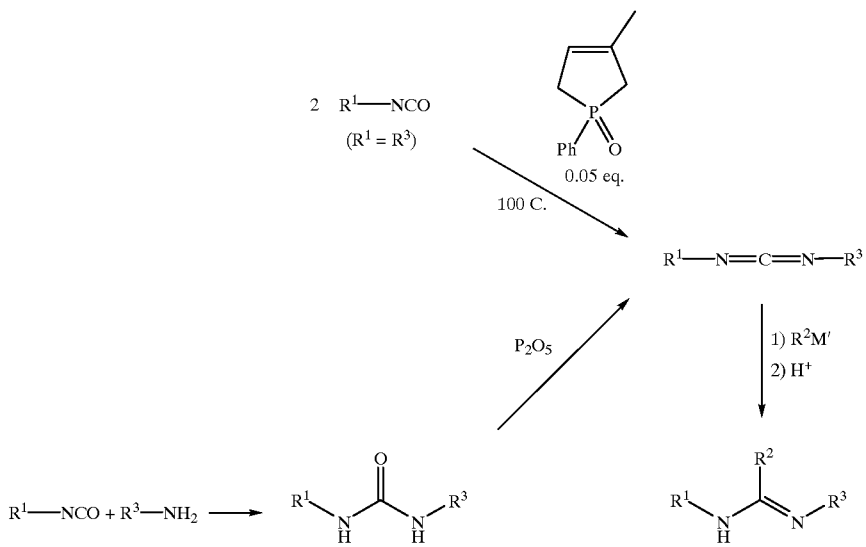

Scheme 1 can be followed at any suitable temperature and in any suitable non-interfering solvent. The process may be run at a temperature from −100° C. to 300° C. Solvent choices include hexane, methylenechloride, dichlorobenzene, benzene, toluene, THF, alcohols, ethers and combinations thereof.

Ancillary ligands may be prepared following scheme 1 from any combination of the following nucleophiles in Table 1 with the carbodiimides in Table 2.

TABLE 1

TABLE 1-continued

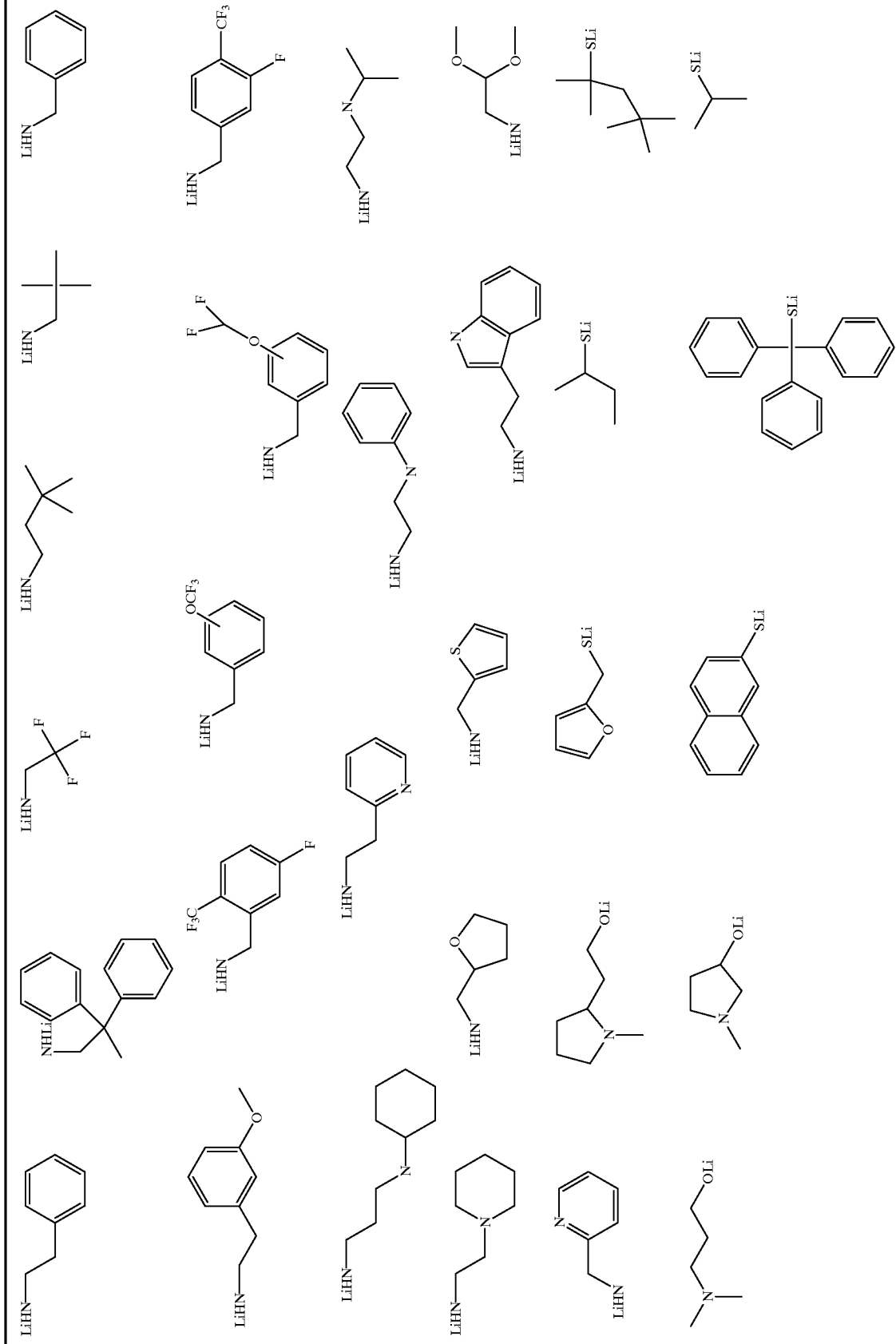

TABLE 1-continued
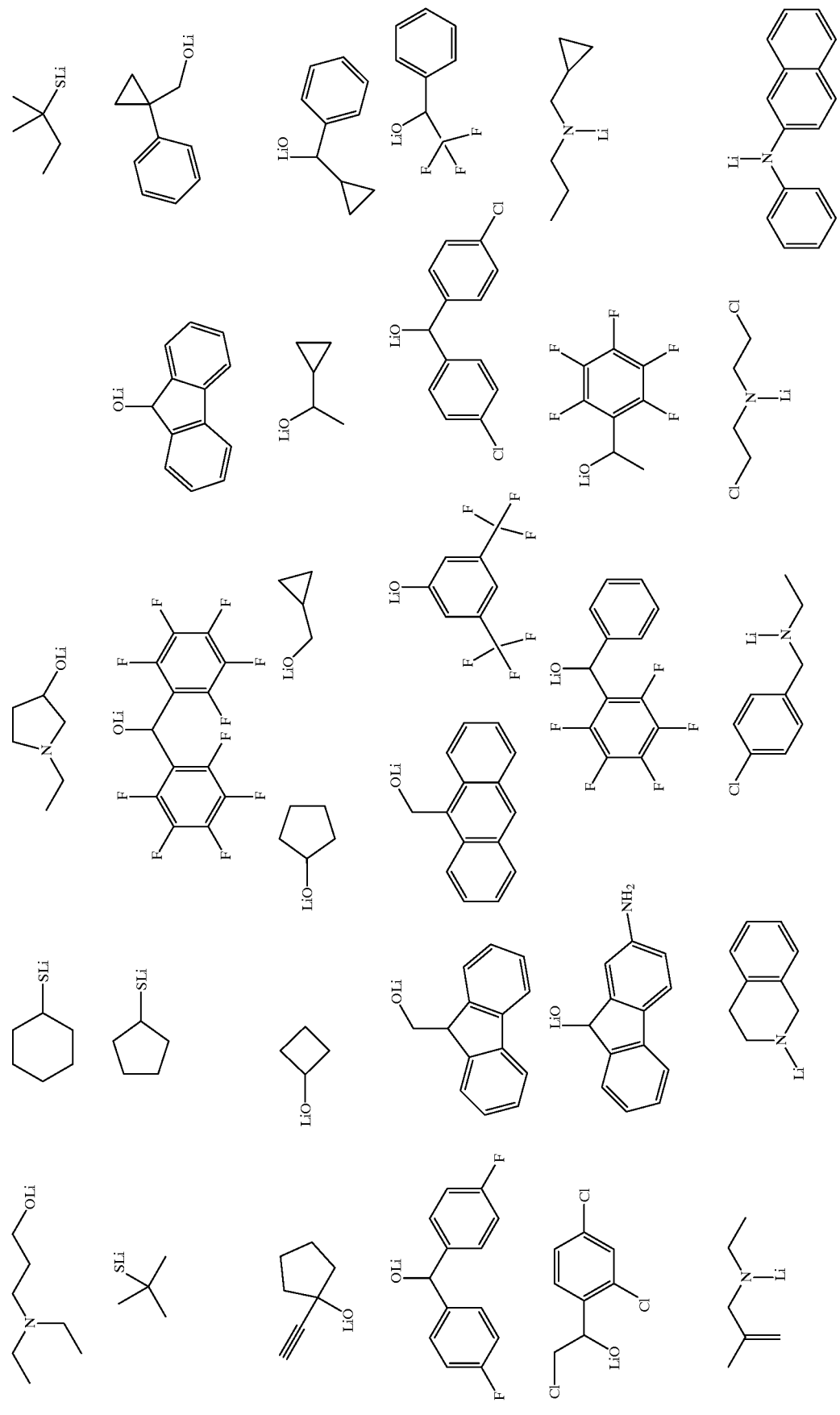

TABLE 1-continued
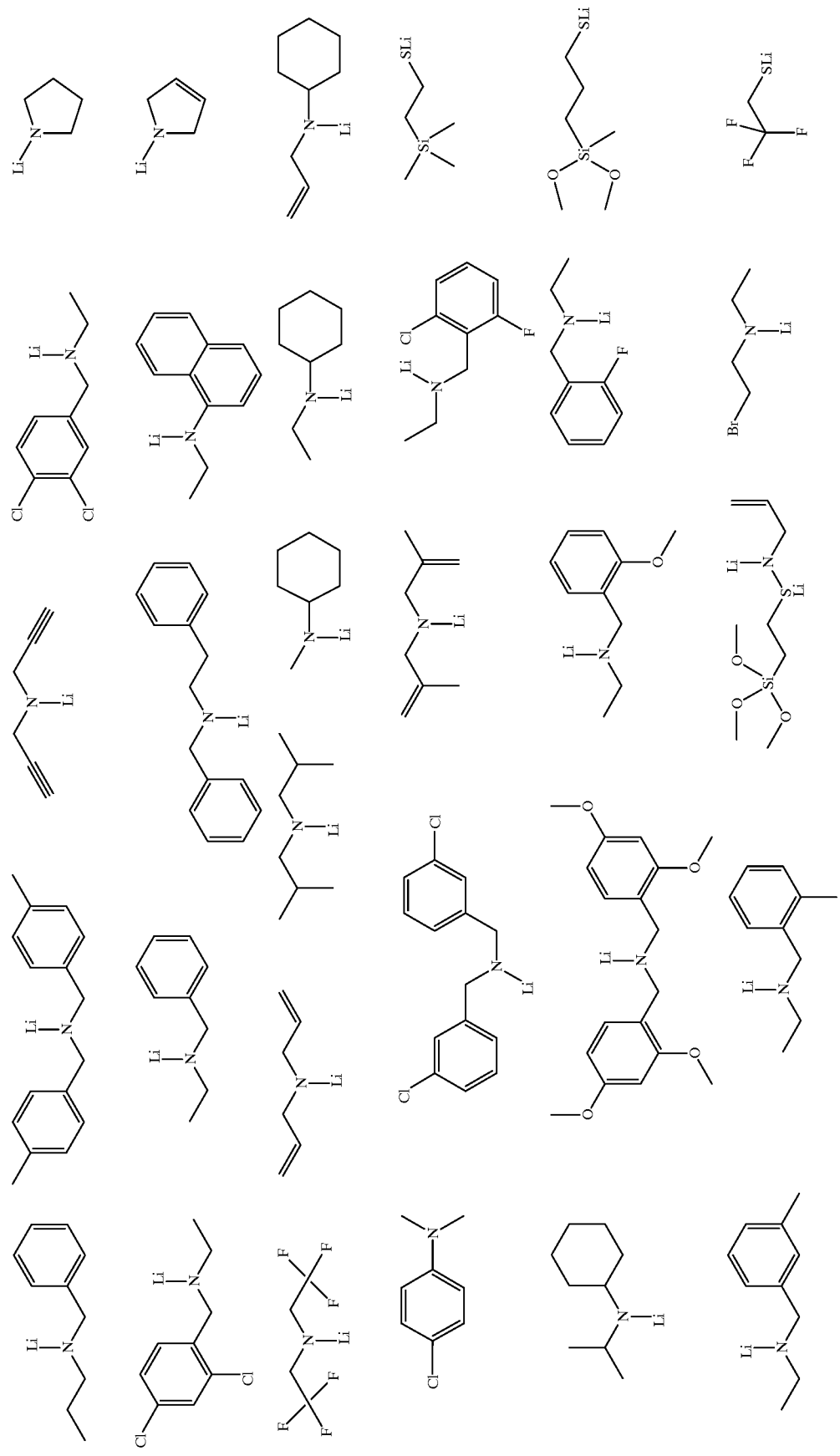

TABLE 1-continued
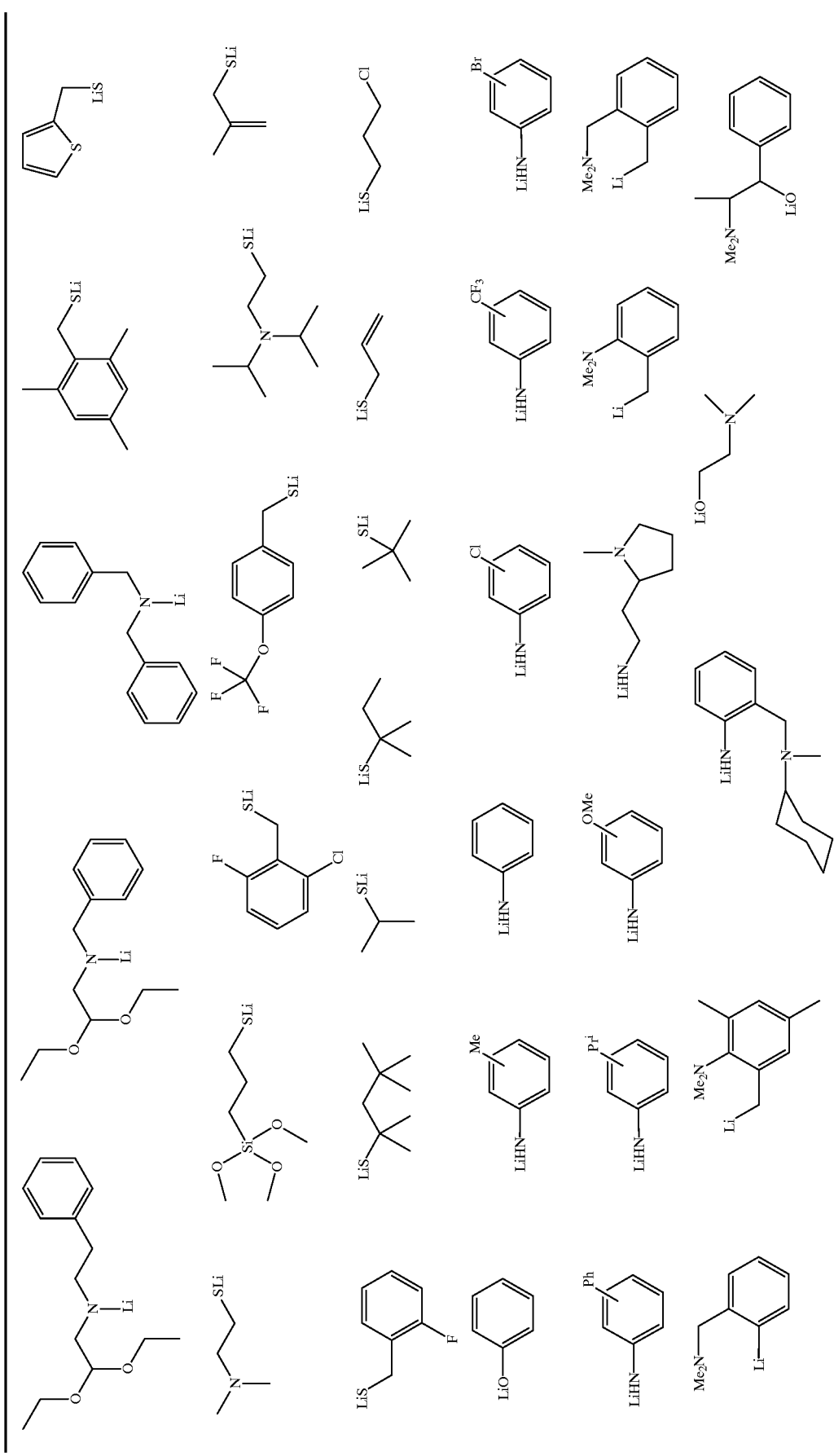

TABLE 1-continued
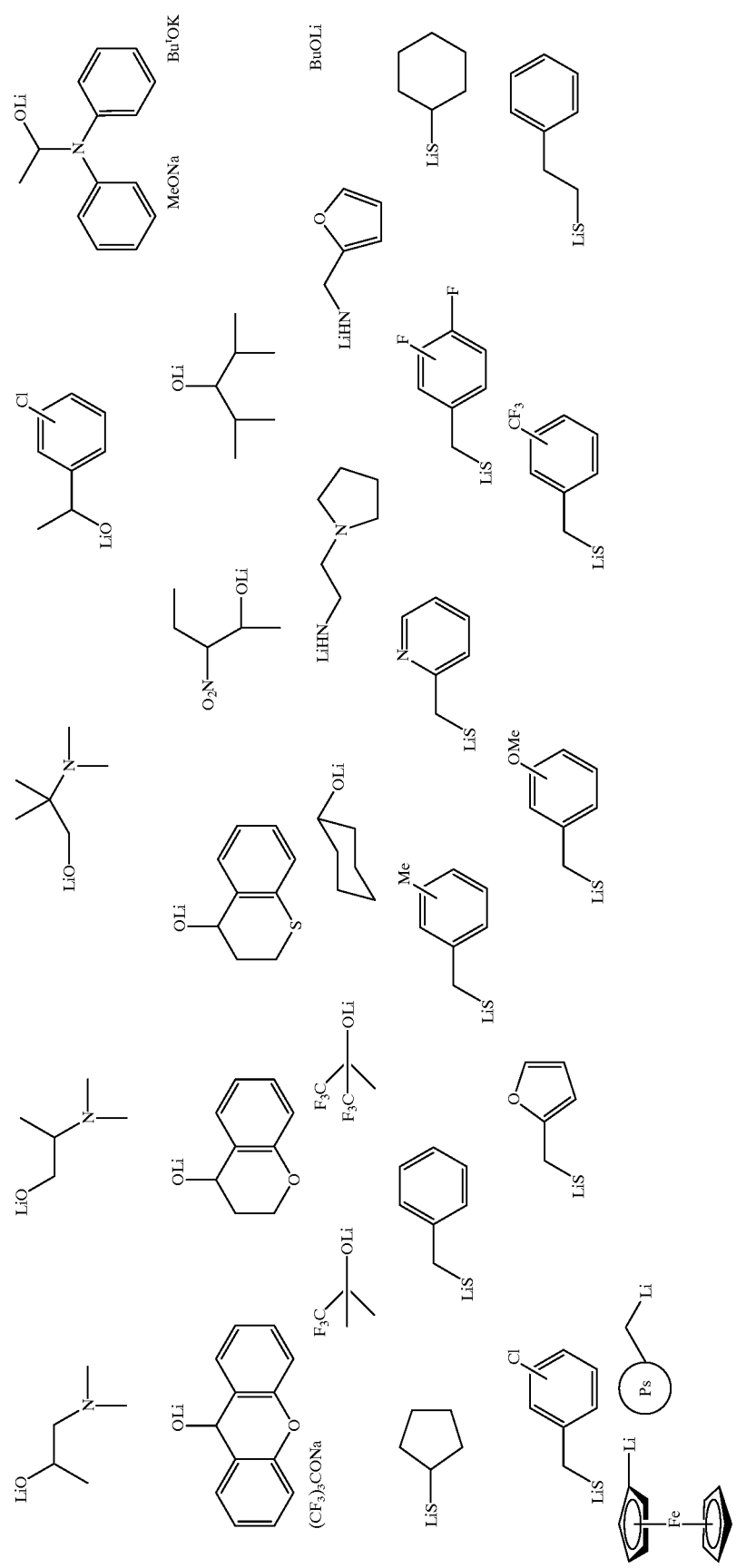

TABLE 2
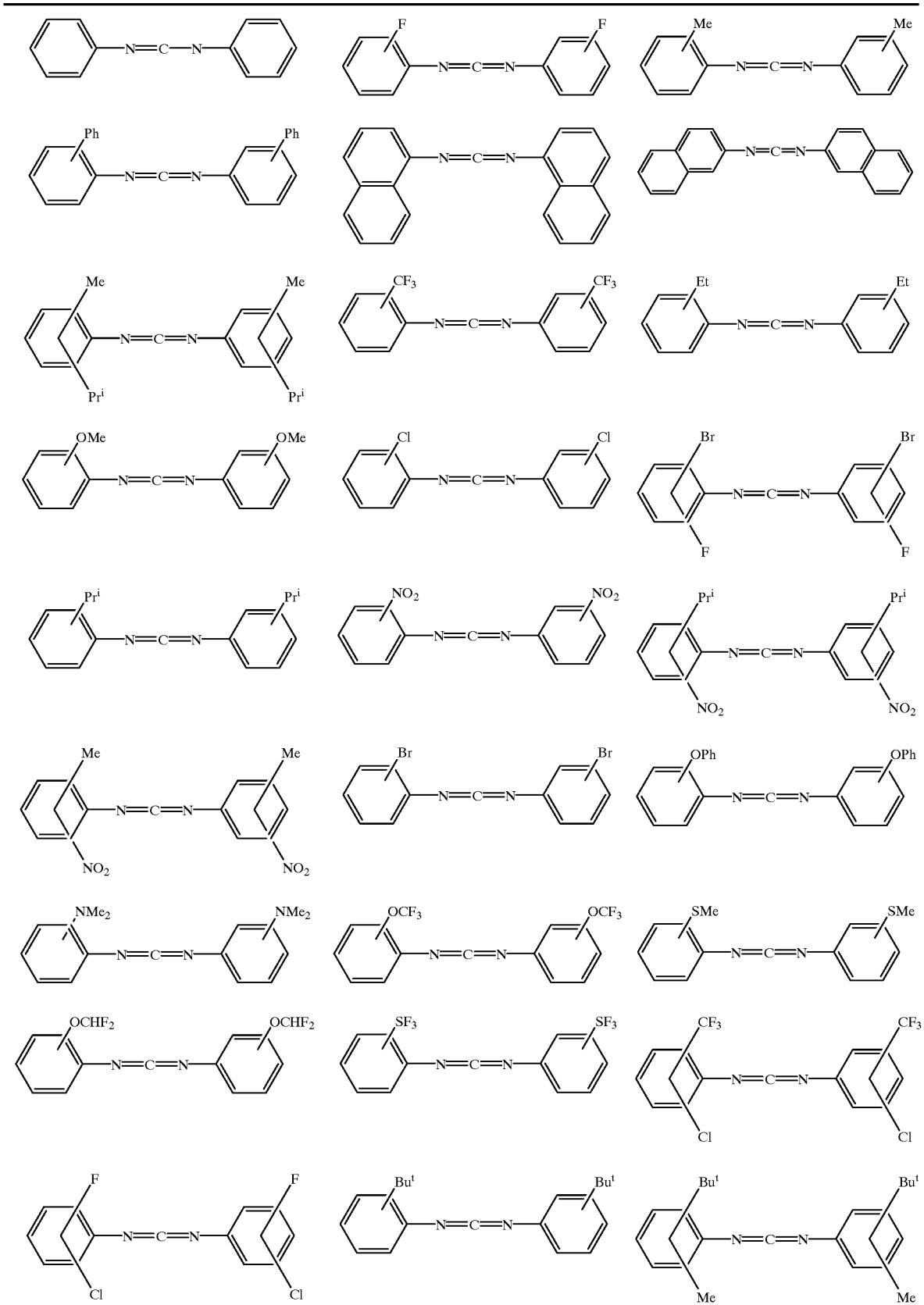

TABLE 2-continued
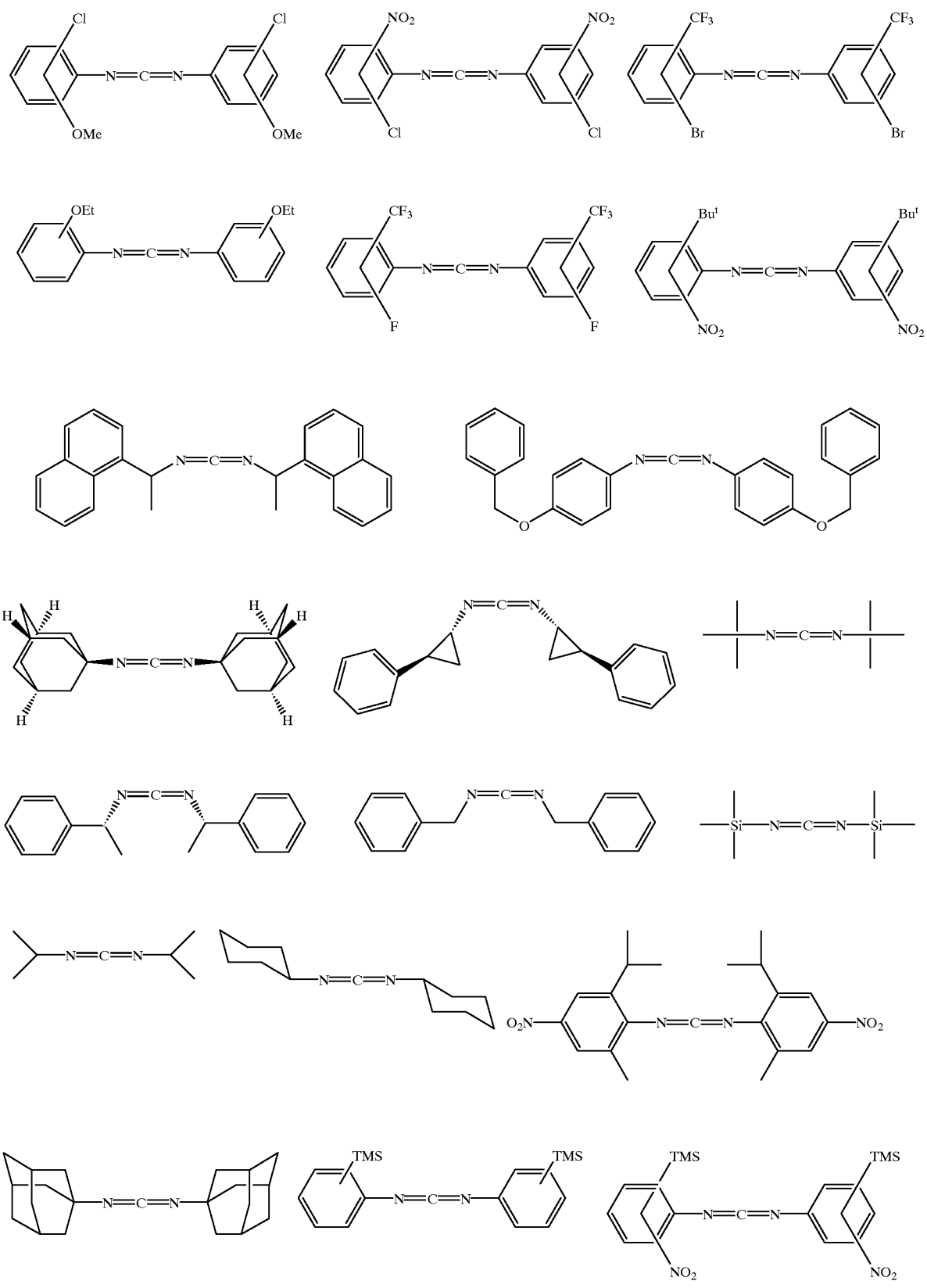

Further optionally, asymmetrically substituted carbodiimides (having the general formula R'-N=C=N-R³ and prepared as outlined in Scheme 1) may be combined with any of the nucleophiles listed in Table 1.
Ancillary ligands that are illustrative of the results of combining reagents from Tables 1 and 2 are listed in Table 3.
TABLE 3
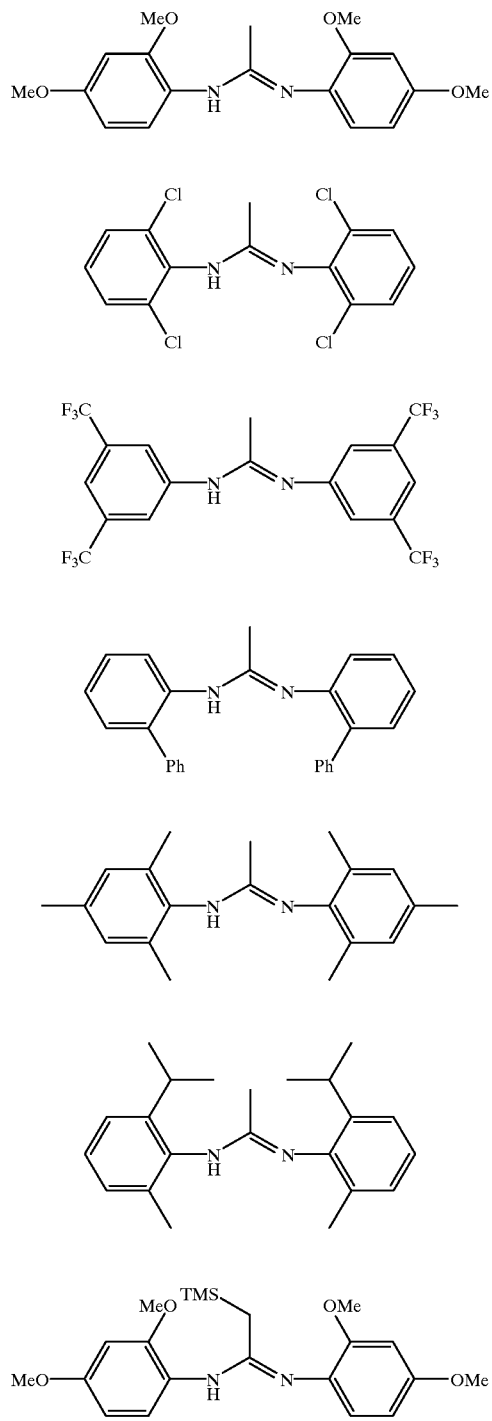
TABLE 3-continued
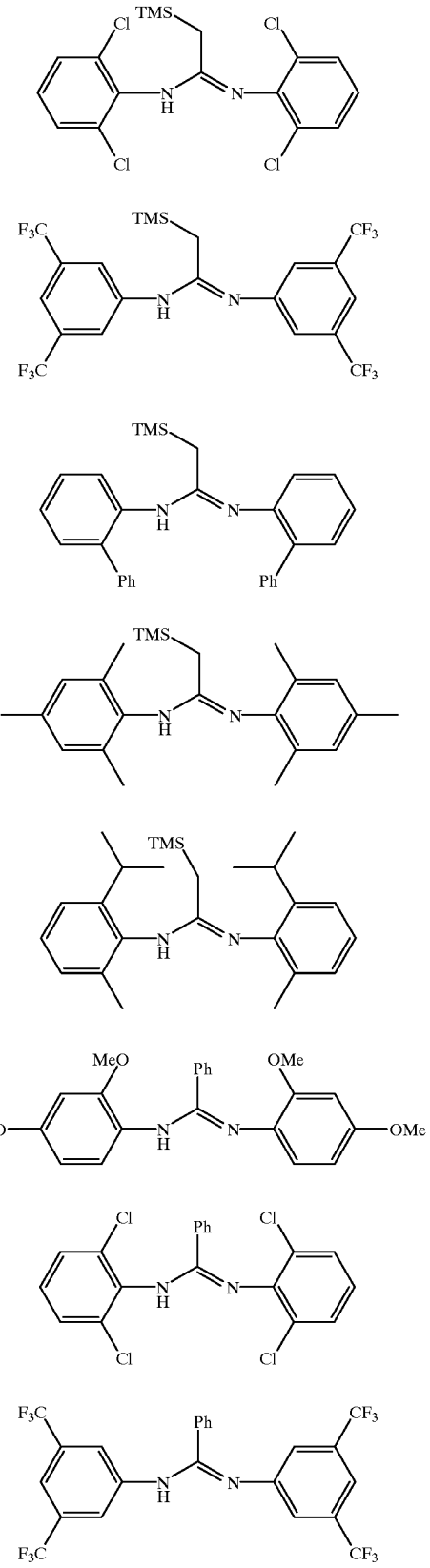

TABLE 3-continued
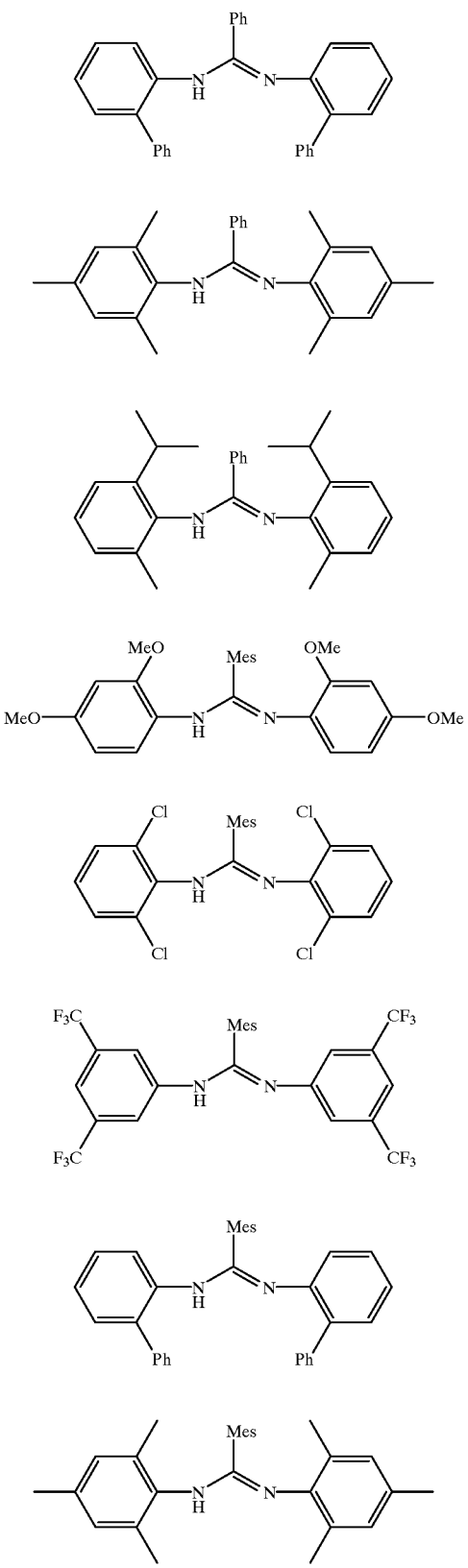
TABLE 3-continued
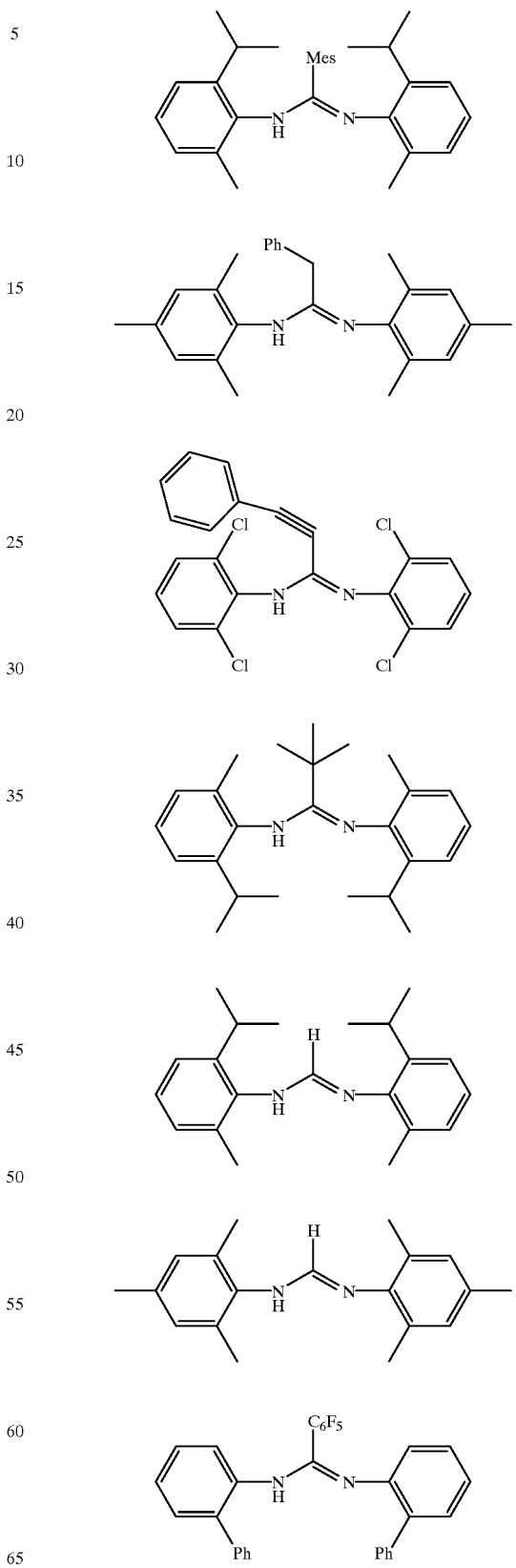

TABLE 3-continued
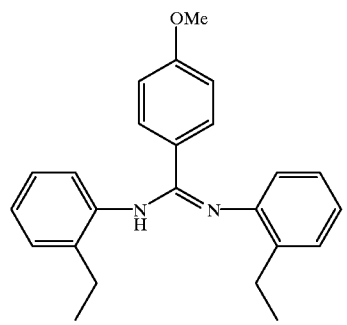
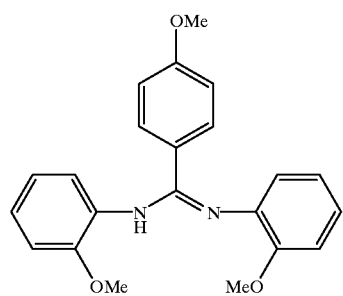
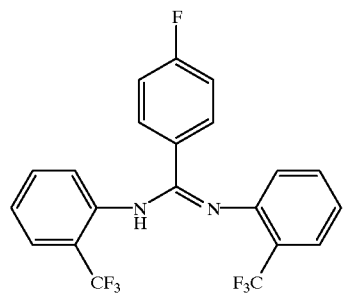
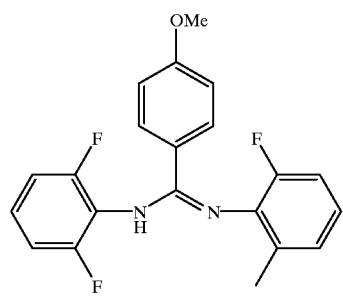
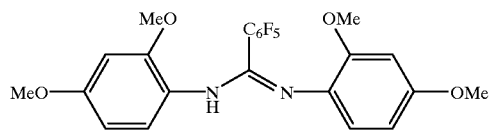
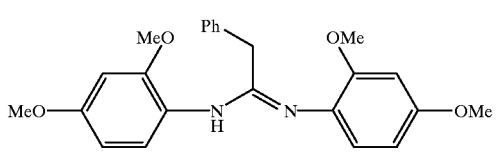
TABLE 3-continued
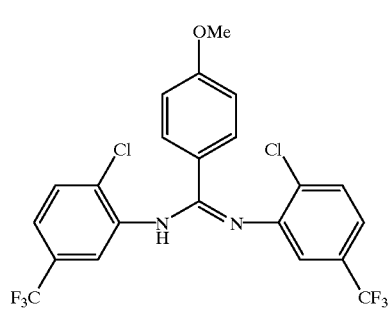
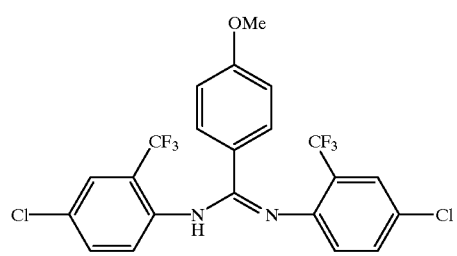
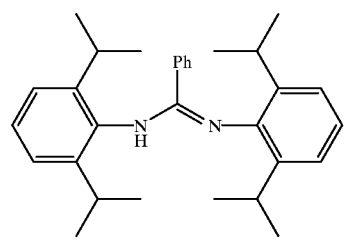
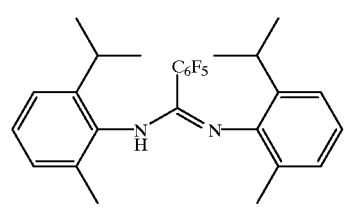
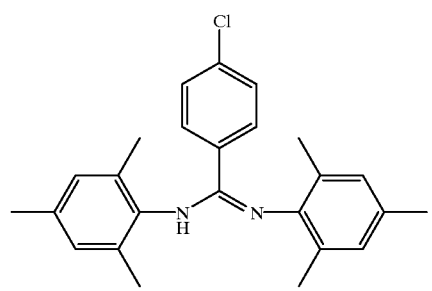

TABLE 3-continued
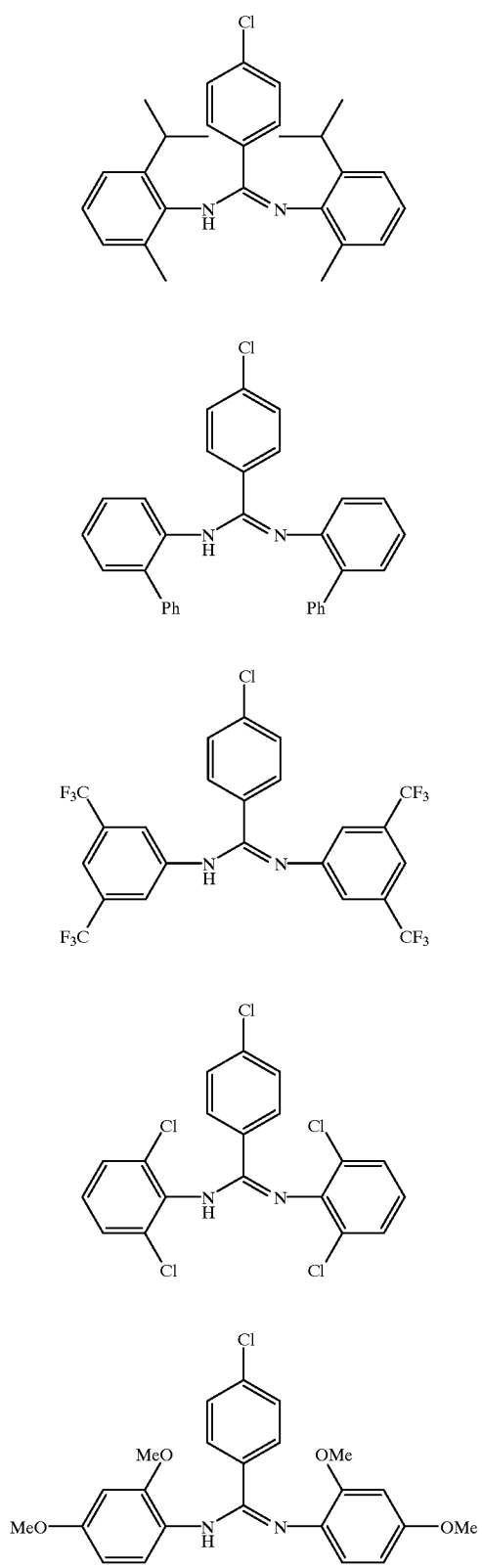
TABLE 3-continued
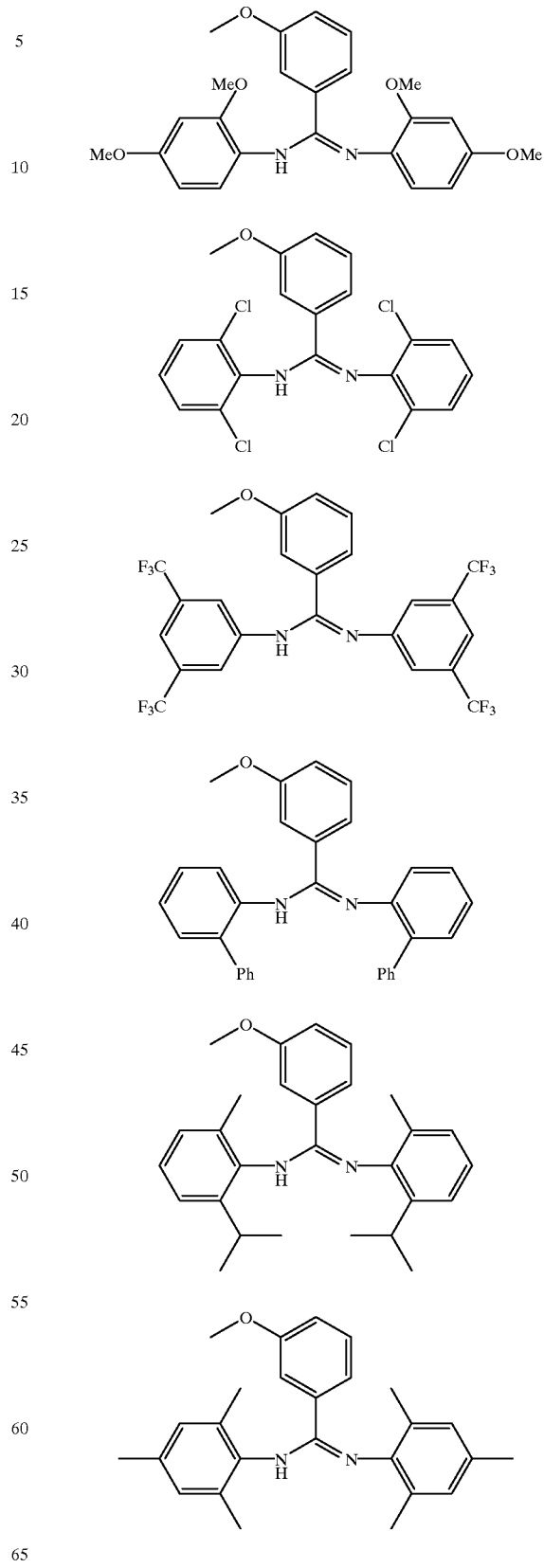

TABLE 3-continued
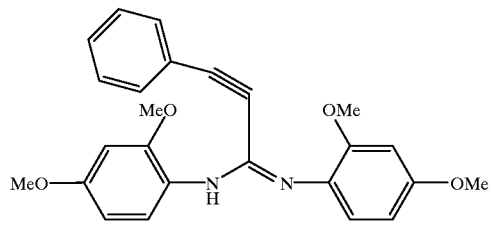
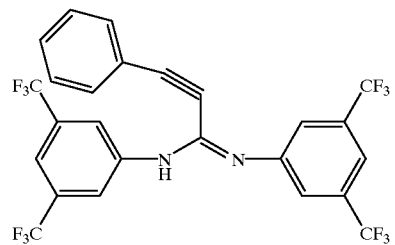
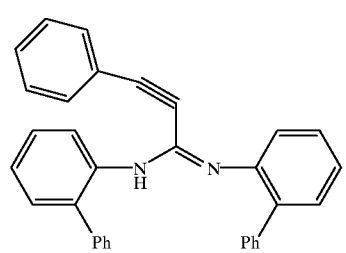
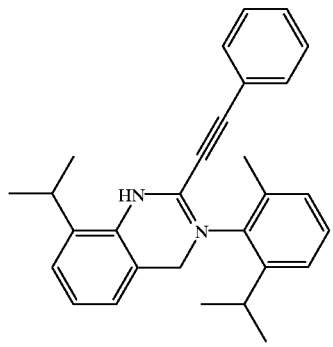
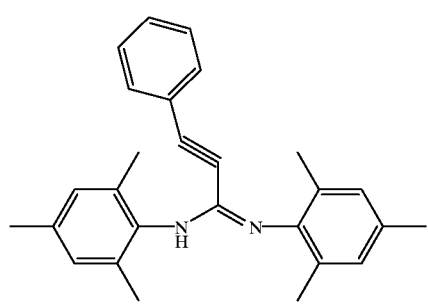
TABLE 3-continued
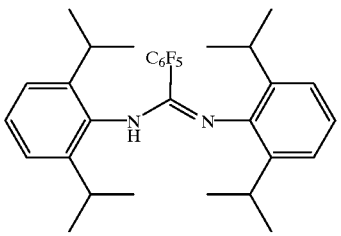
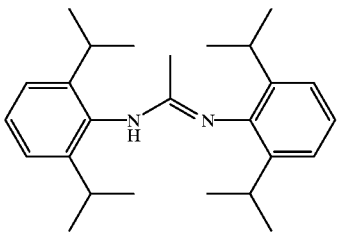
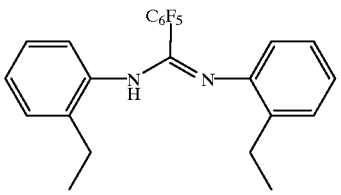
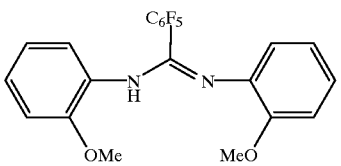
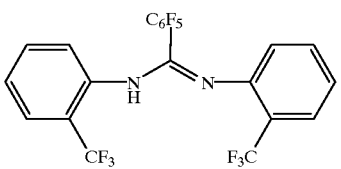
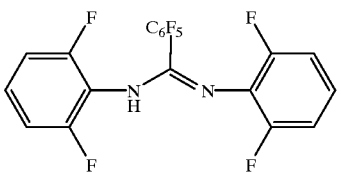
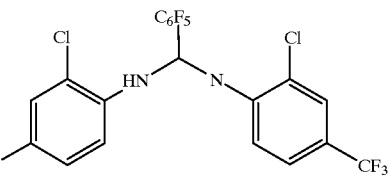

TABLE 3-continued
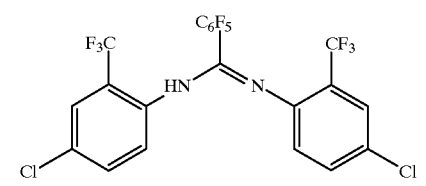
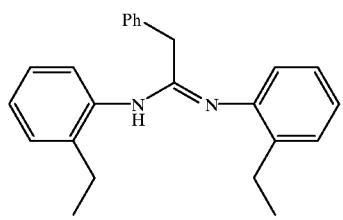
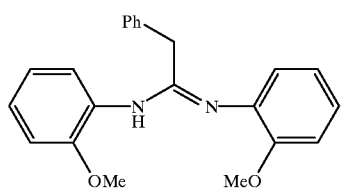
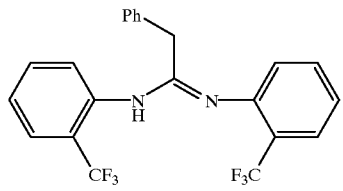
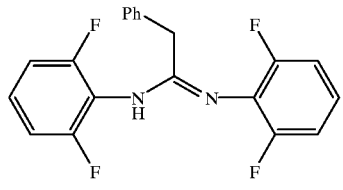
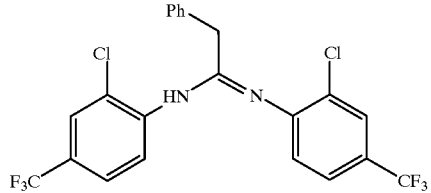
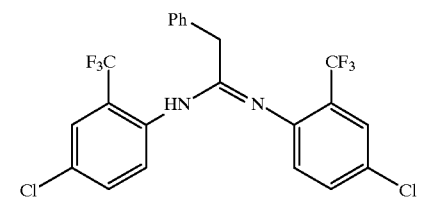
TABLE 3-continued
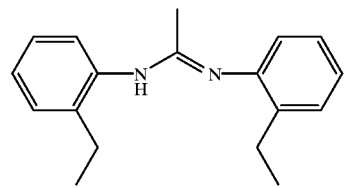
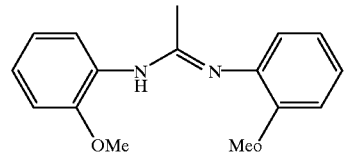
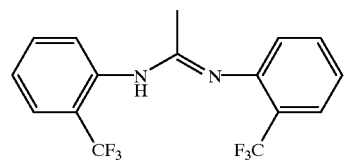
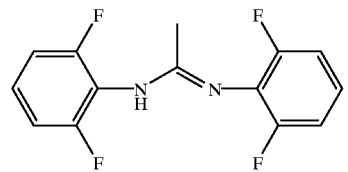
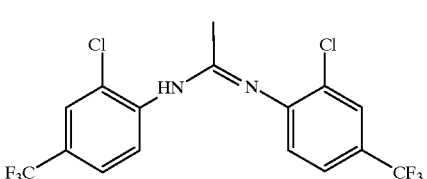
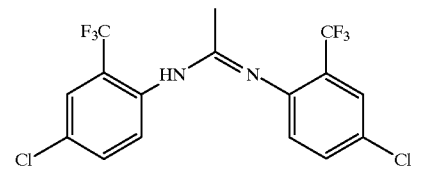
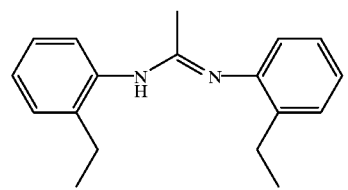
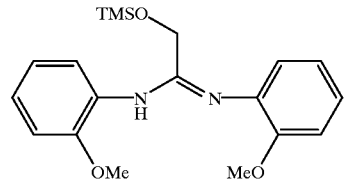

TABLE 3-continued
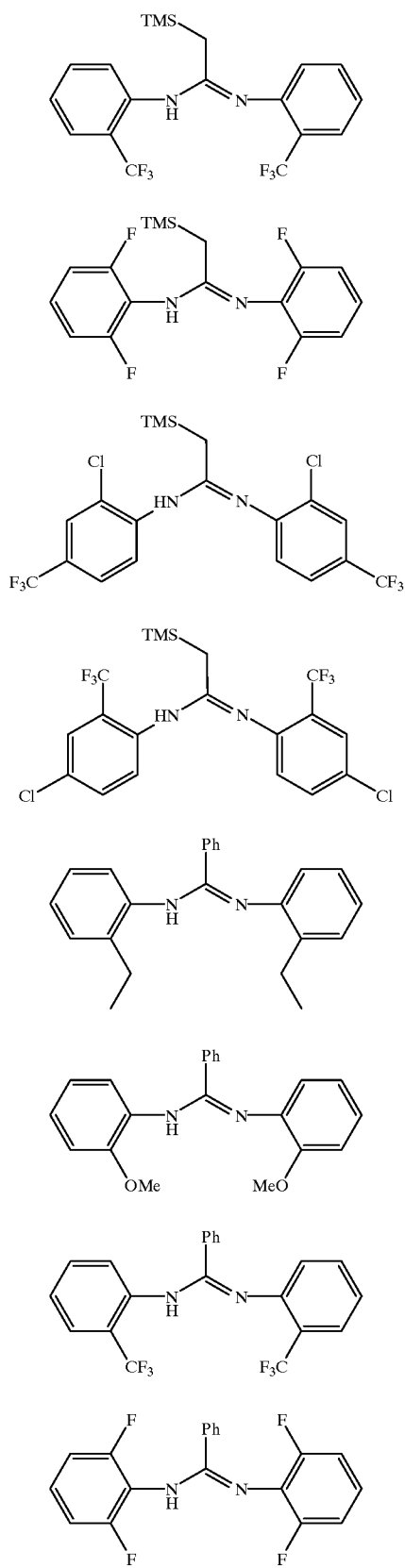
TABLE 3-continued
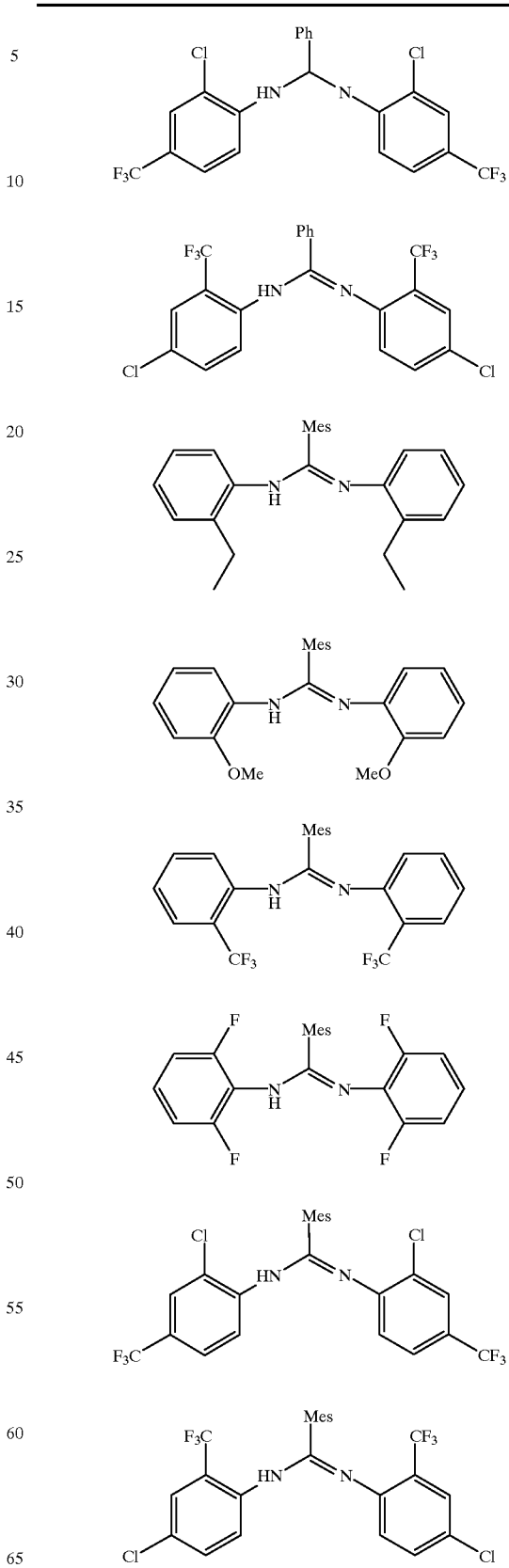

TABLE 3-continued
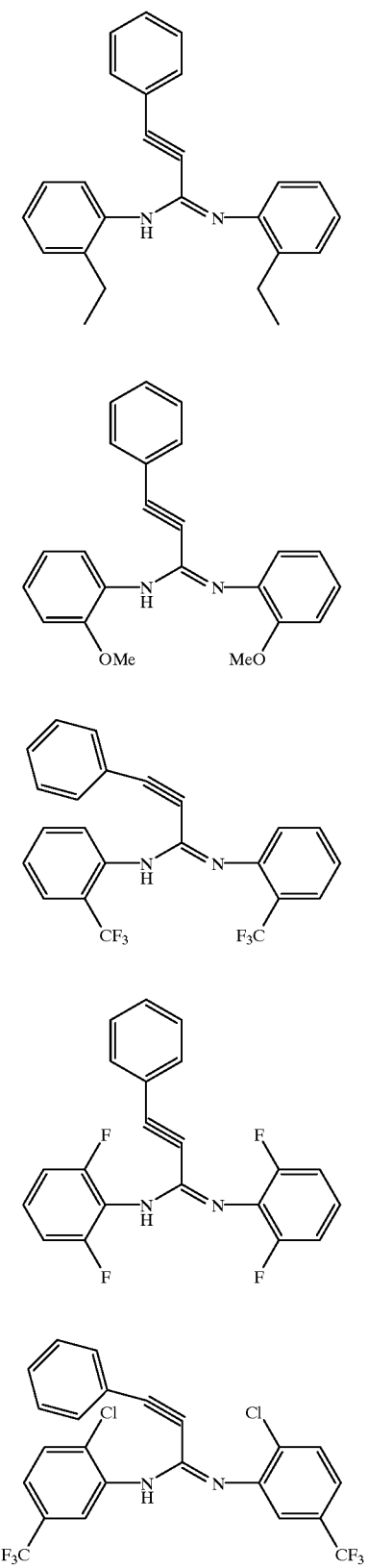
TABLE 3-continued
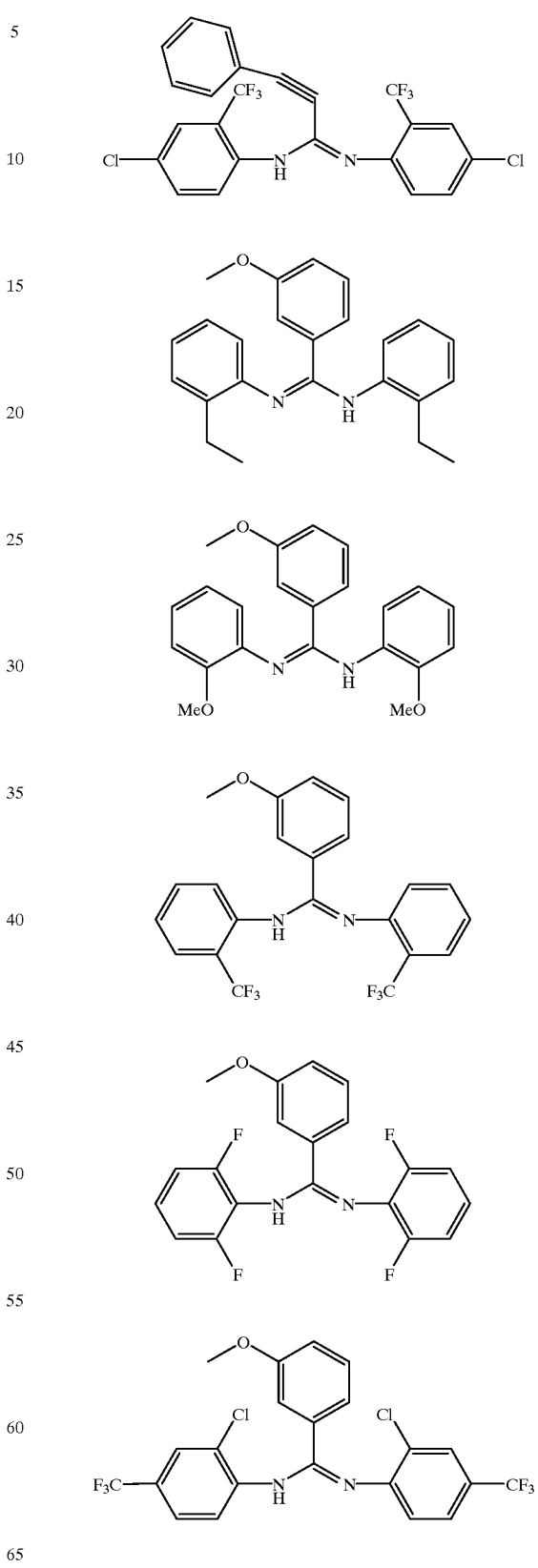

TABLE 3-continued
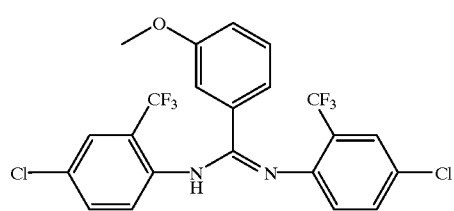
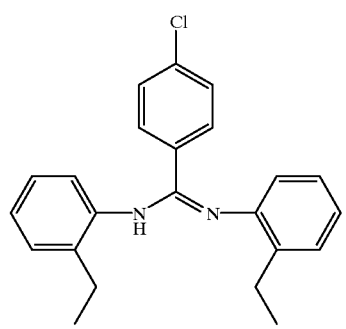
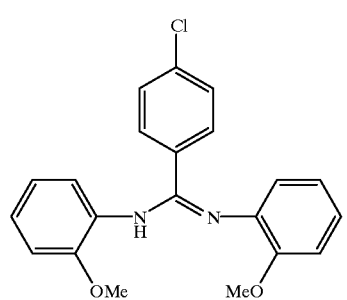
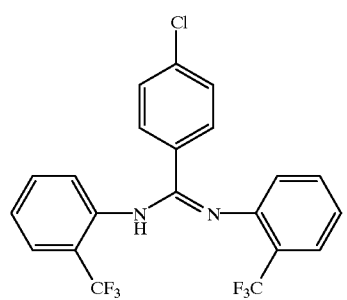
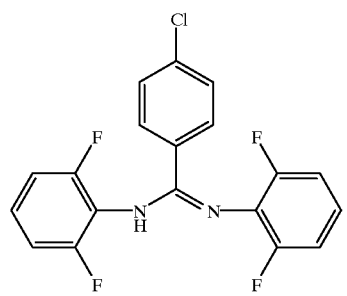
TABLE 3-continued
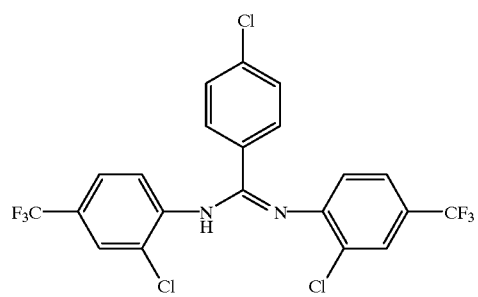
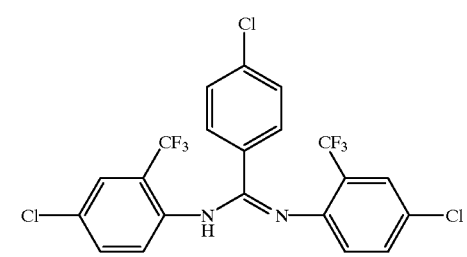
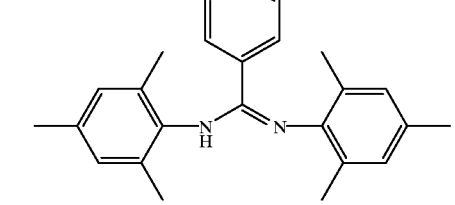
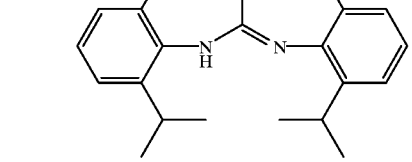
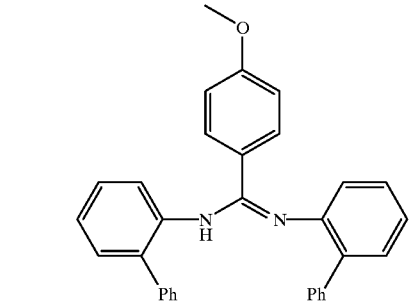

TABLE 3-continued
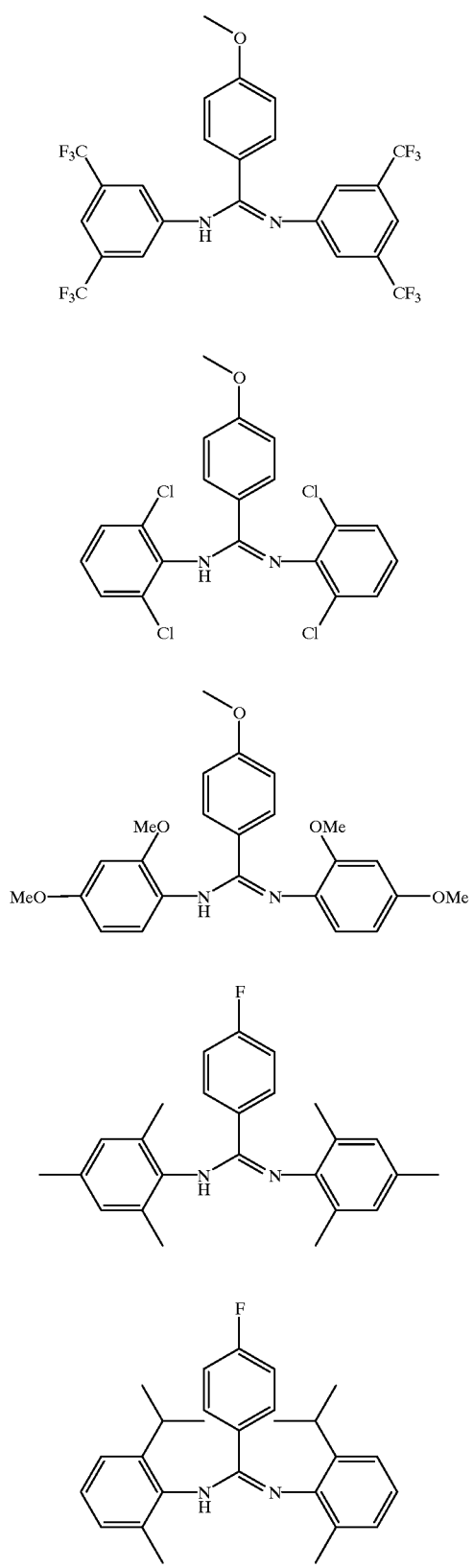
TABLE 3-continued
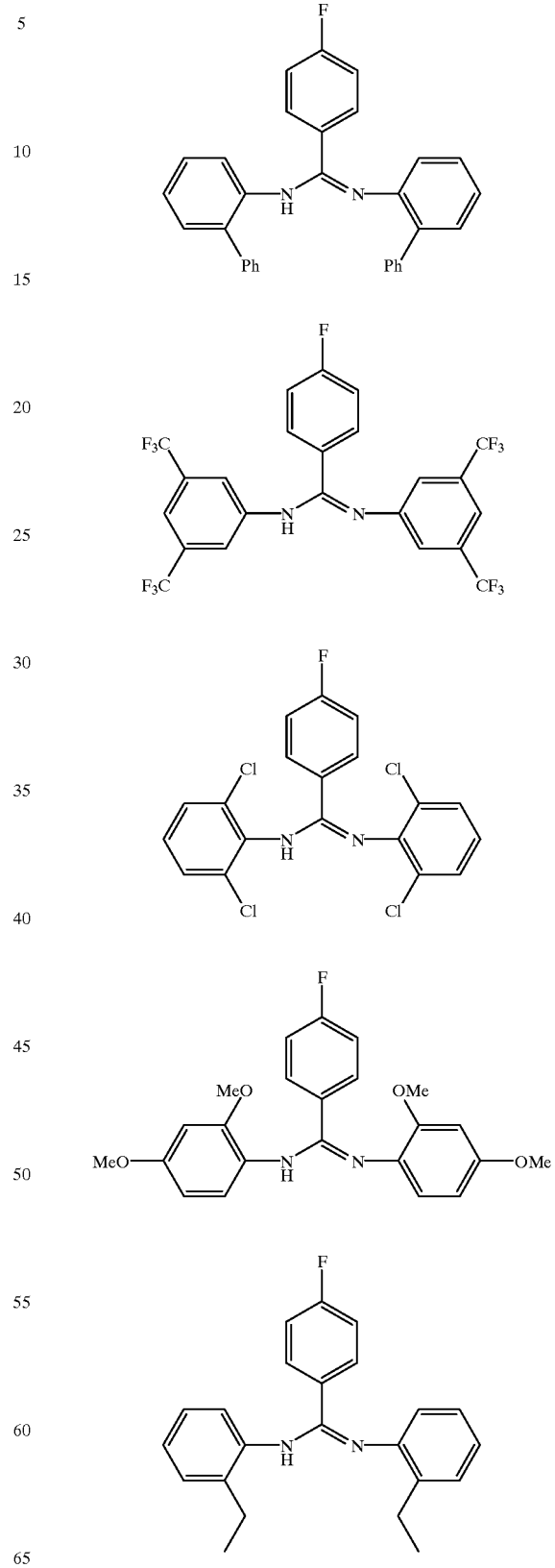

TABLE 3-continued
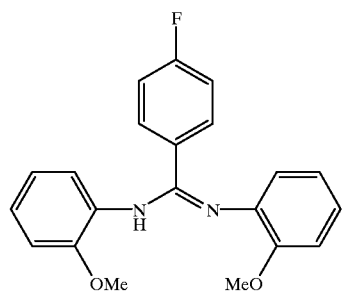
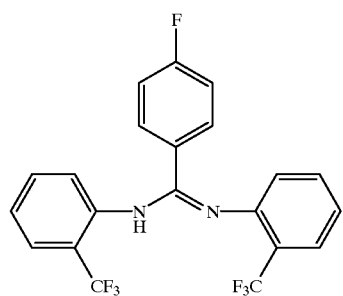
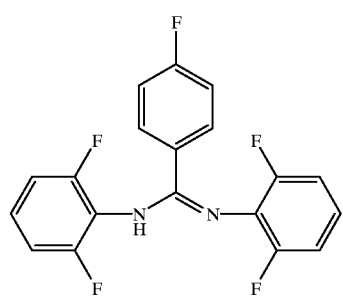
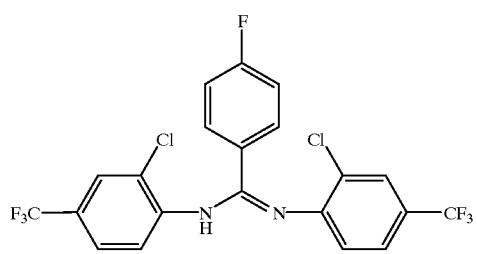
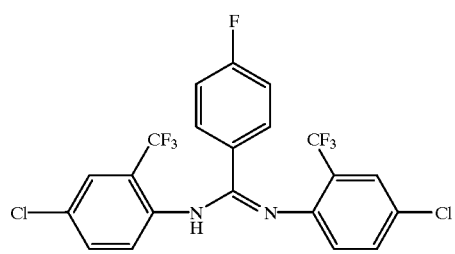
TABLE 3-continued
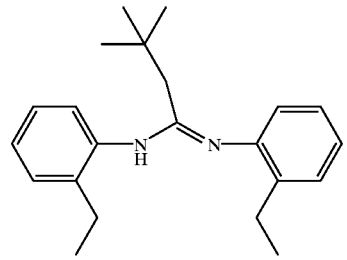
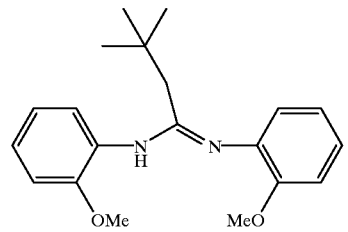
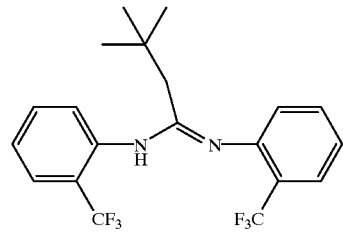
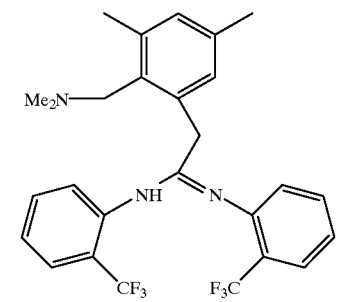
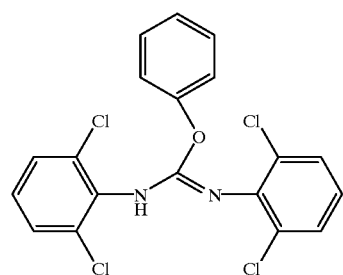
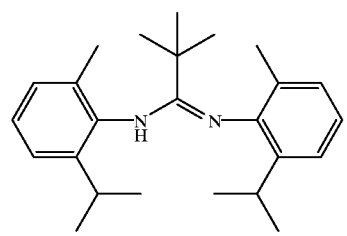

TABLE 3-continued
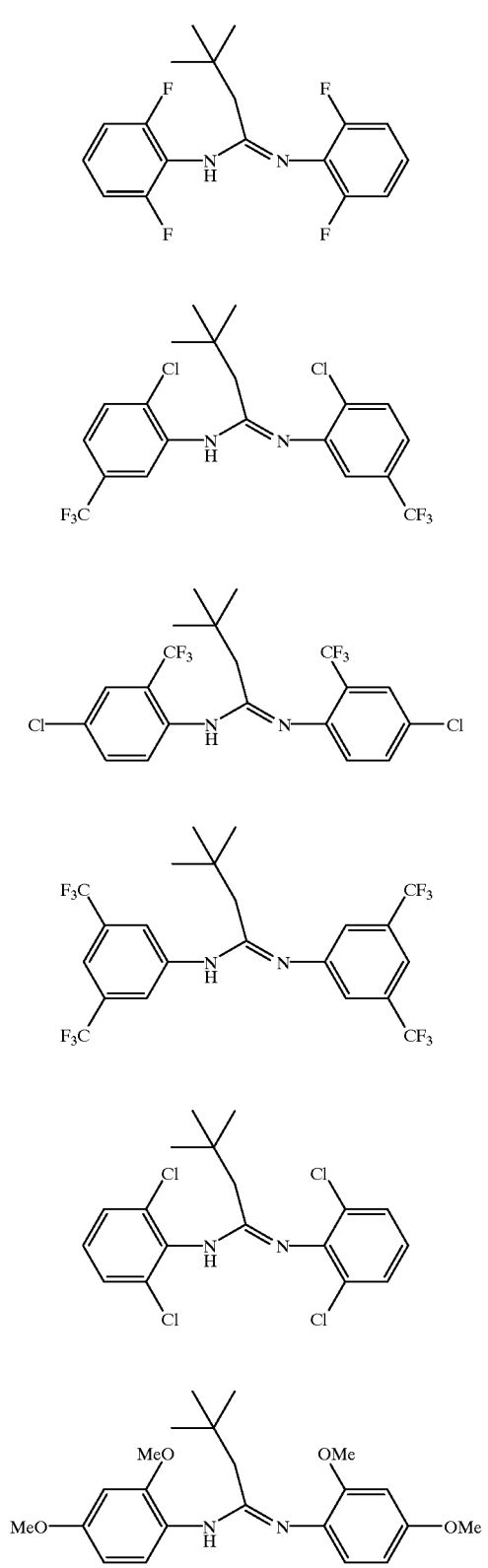
TABLE 3-continued
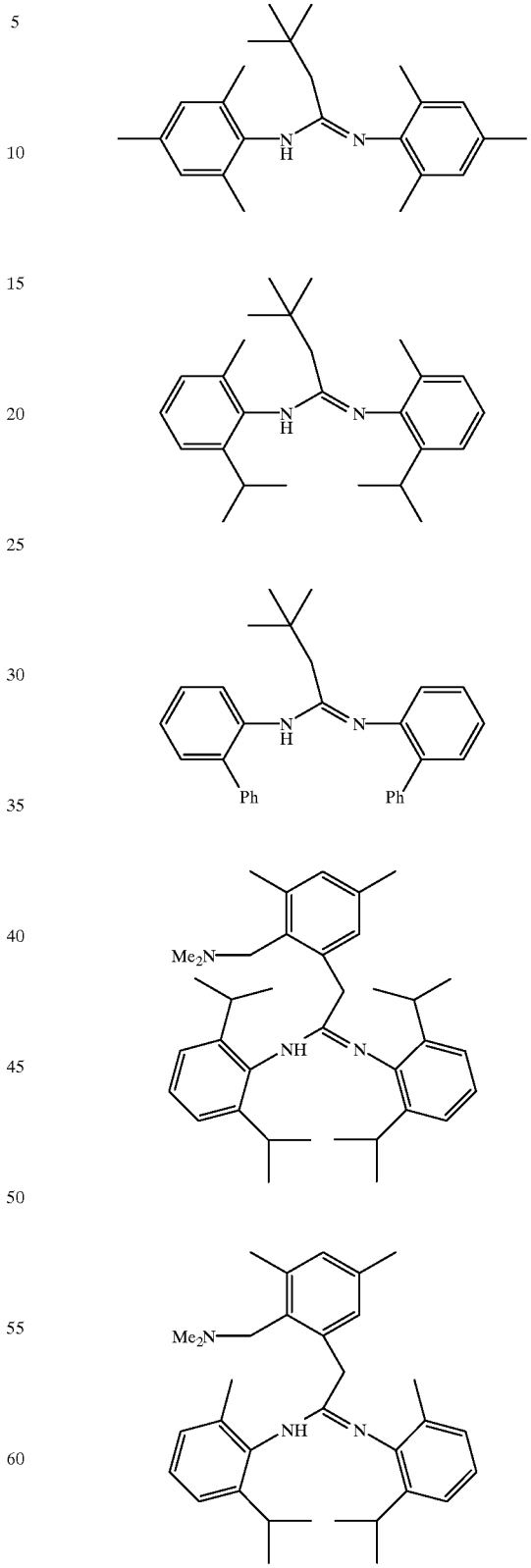

TABLE 3-continued
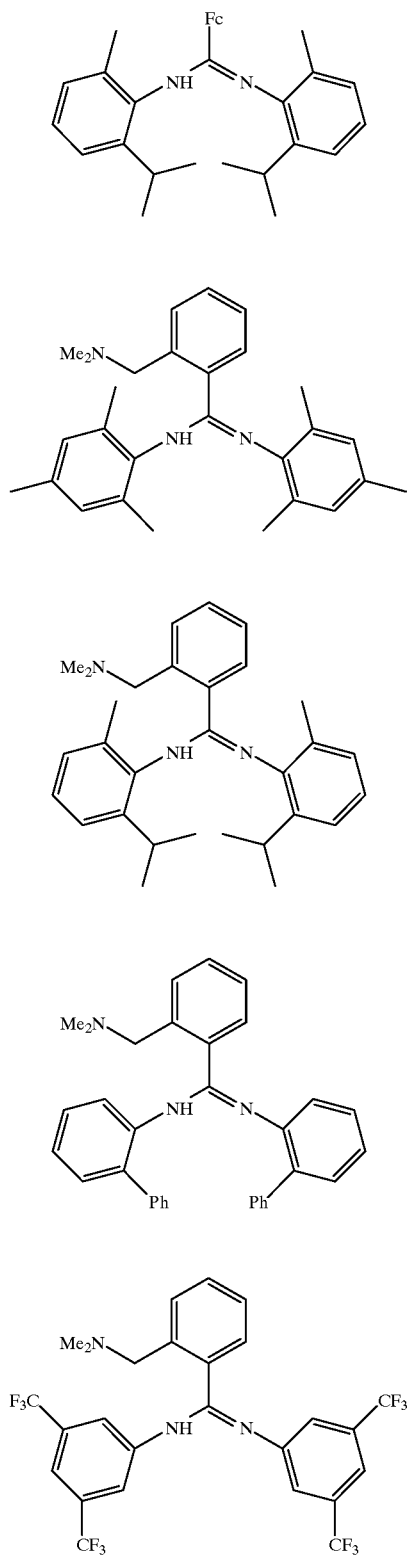
TABLE 3-continued
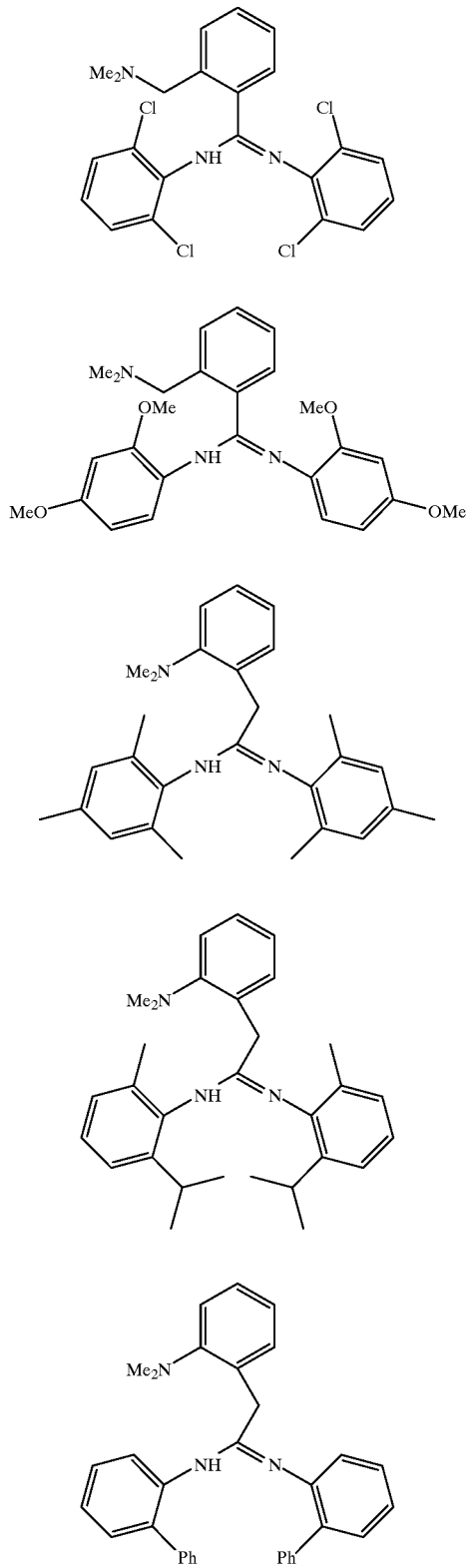

TABLE 3-continued
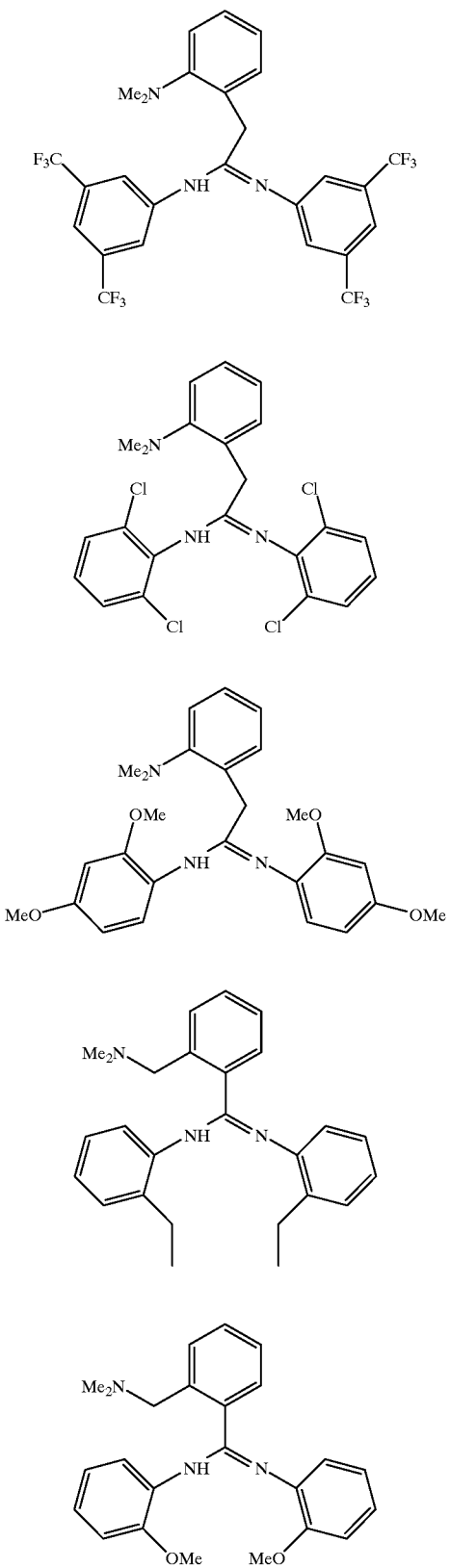
TABLE 3-continued
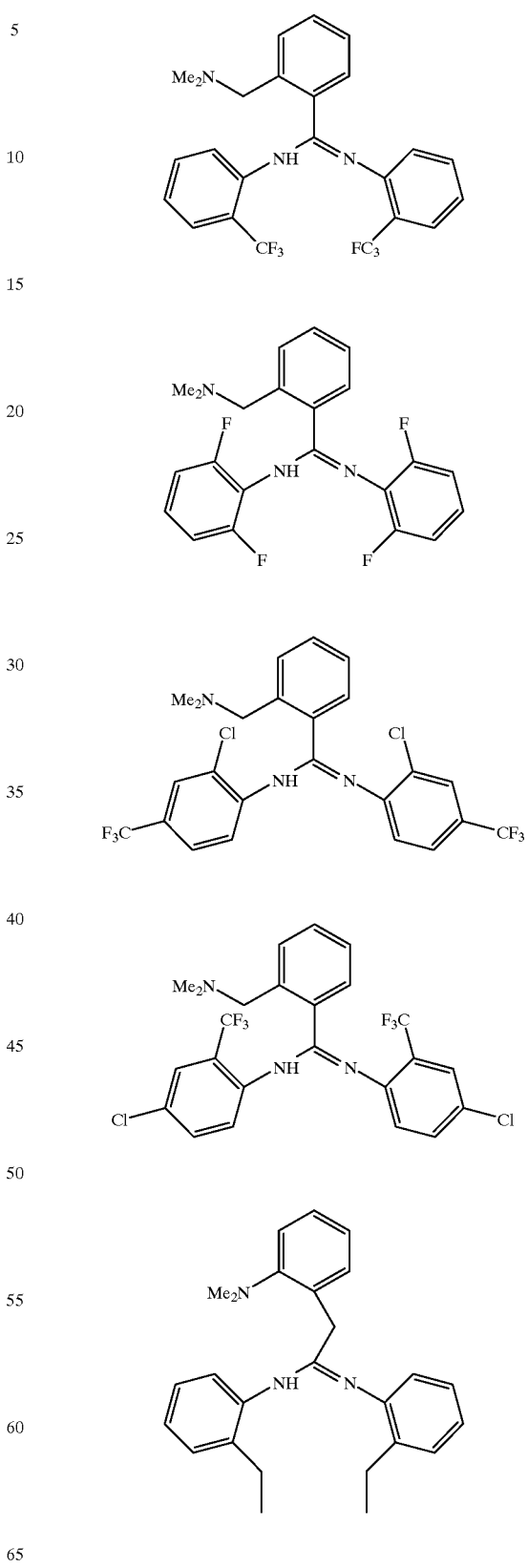

TABLE 3-continued
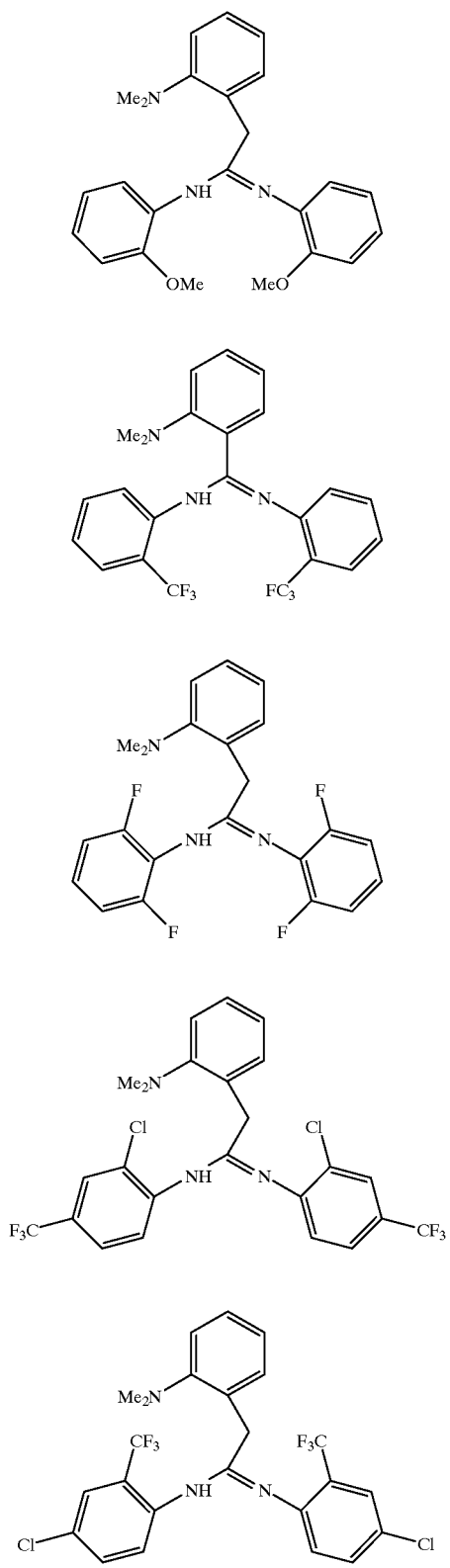
TABLE 3-continued
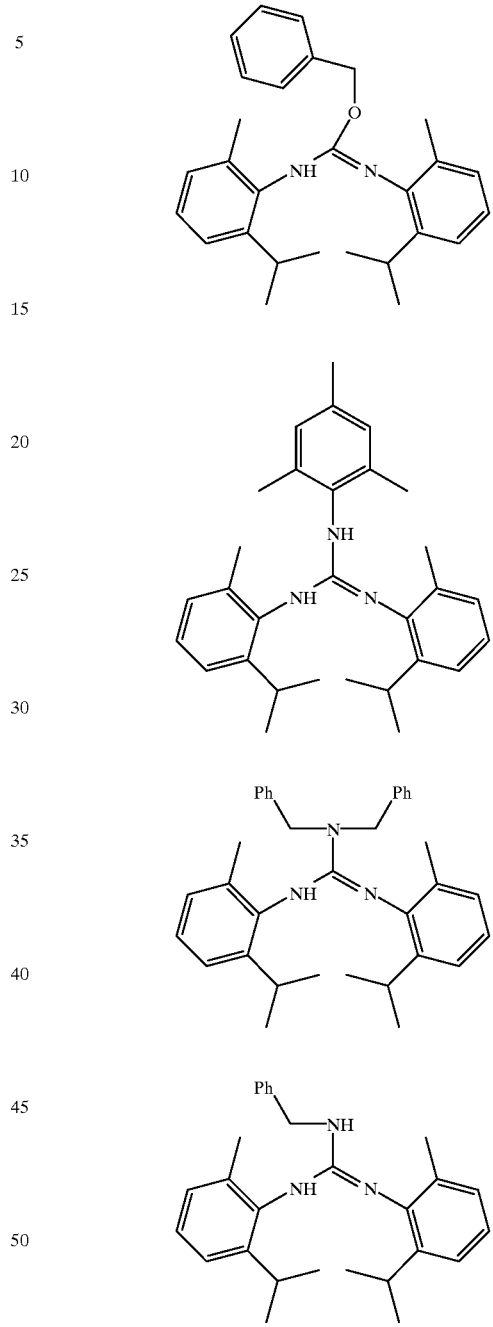
Another example of ancillary ligands of this invention include those ligands that can be represented by the formula:
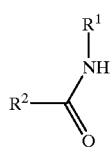
These ancillary ligands are prepared using one of the two following routes outlined below in Scheme 2:

Scheme 2
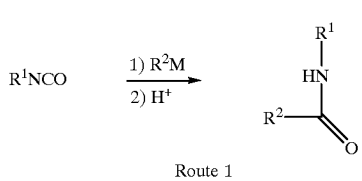
Route 1
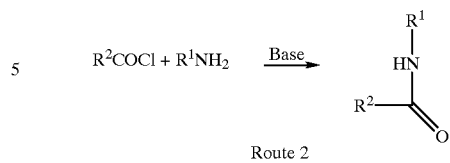
Route 2
Using Route 1 in Scheme 2, the nucleophiles listed in Table 1 are combined with the isocyanates in Table 4, below, to prepare the ancillary ligands:
TABLE 4
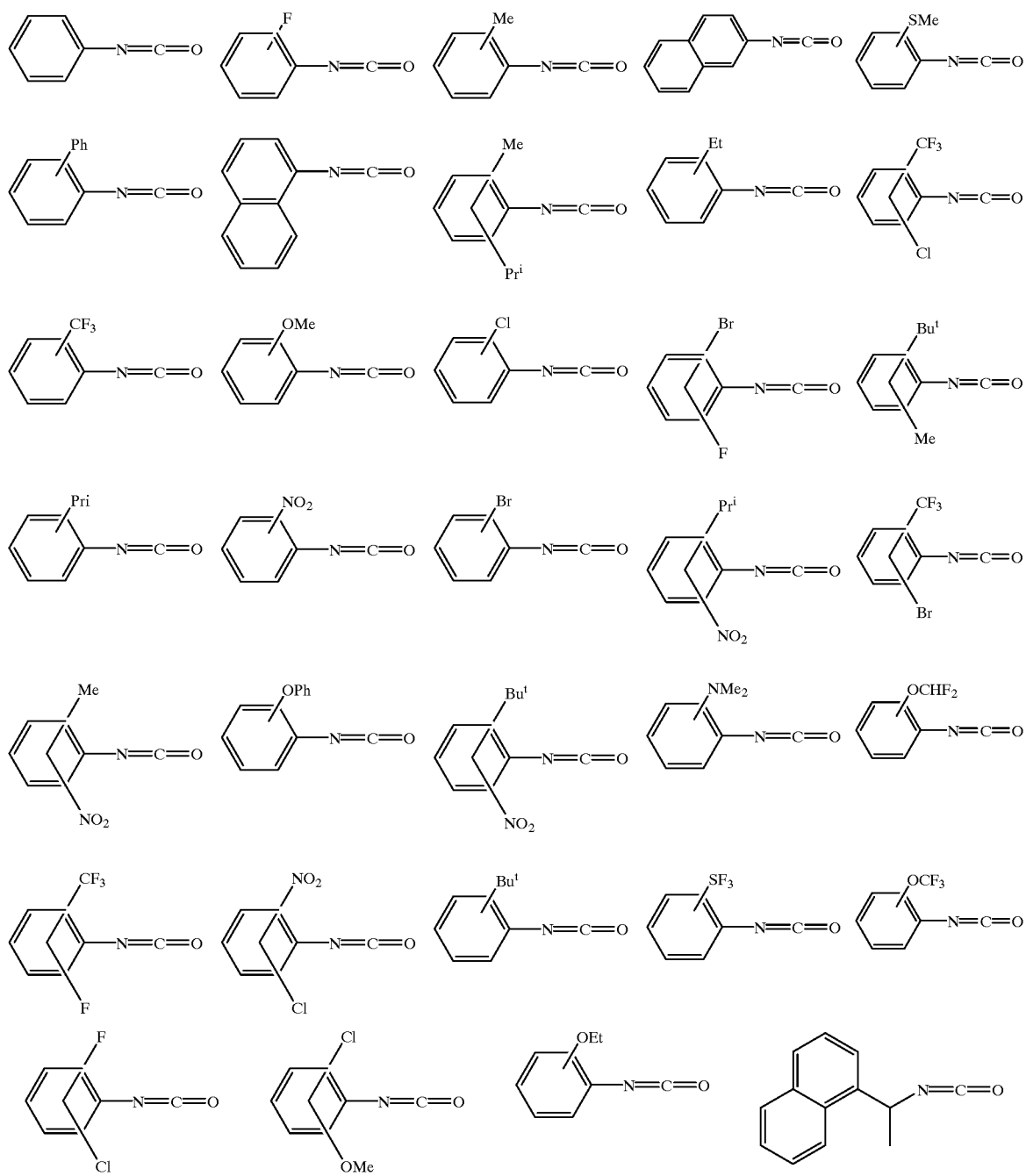

TABLE 4-continued
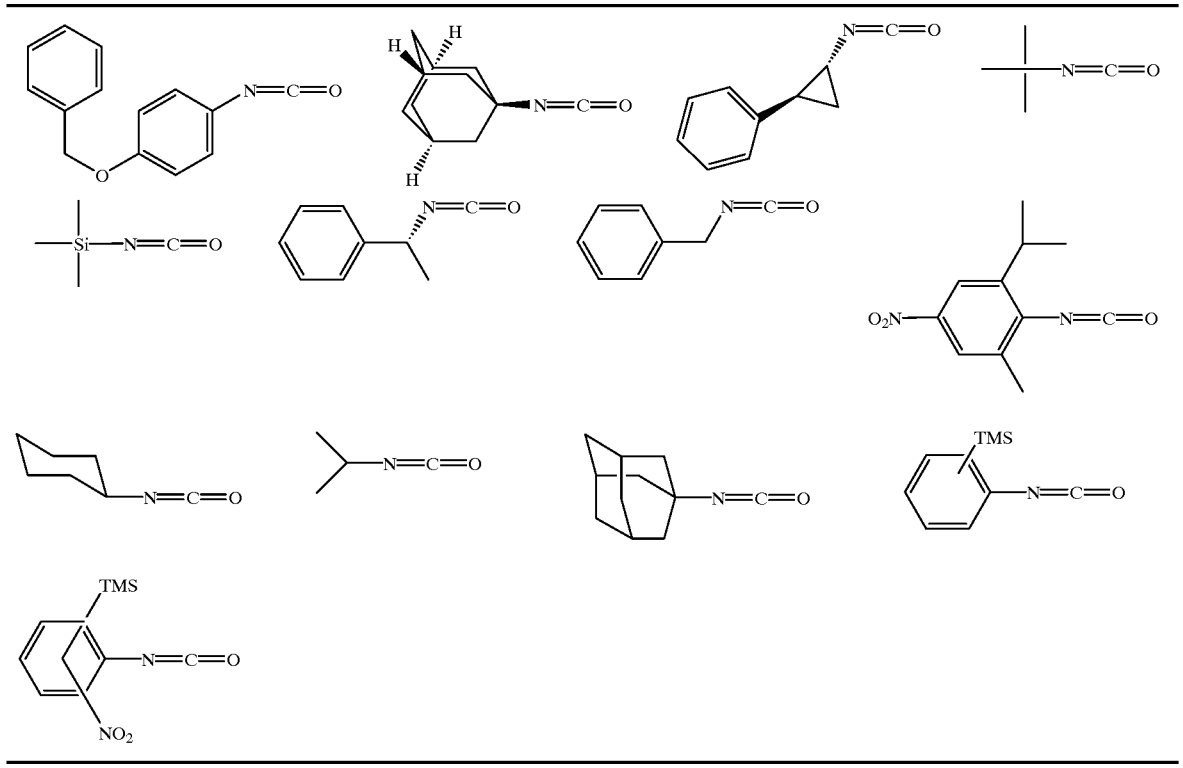
Ancillary ligands that are illustrative of the results of combining reagents from Tables 1 and 4 are listed in Table 5.
TABLE 5
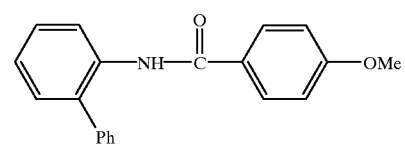
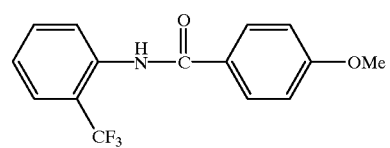
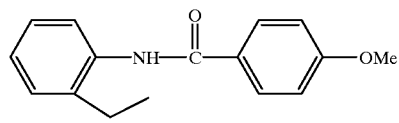
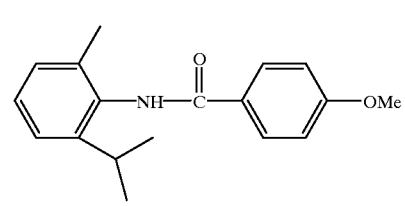
TABLE 5-continued
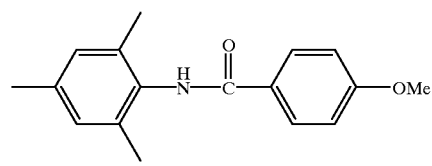
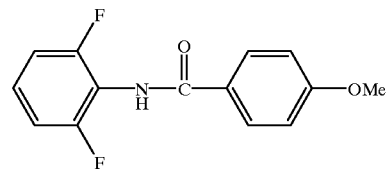
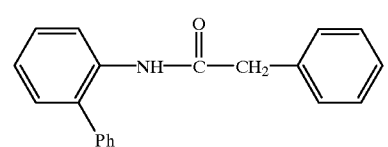
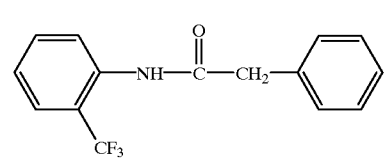

TABLE 5-continued
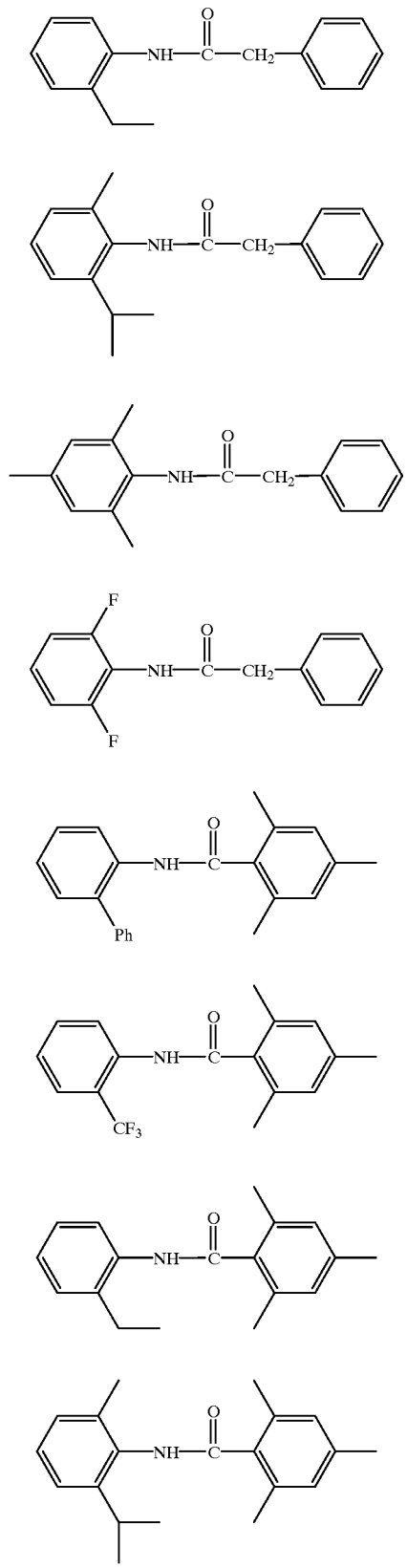
TABLE 5-continued
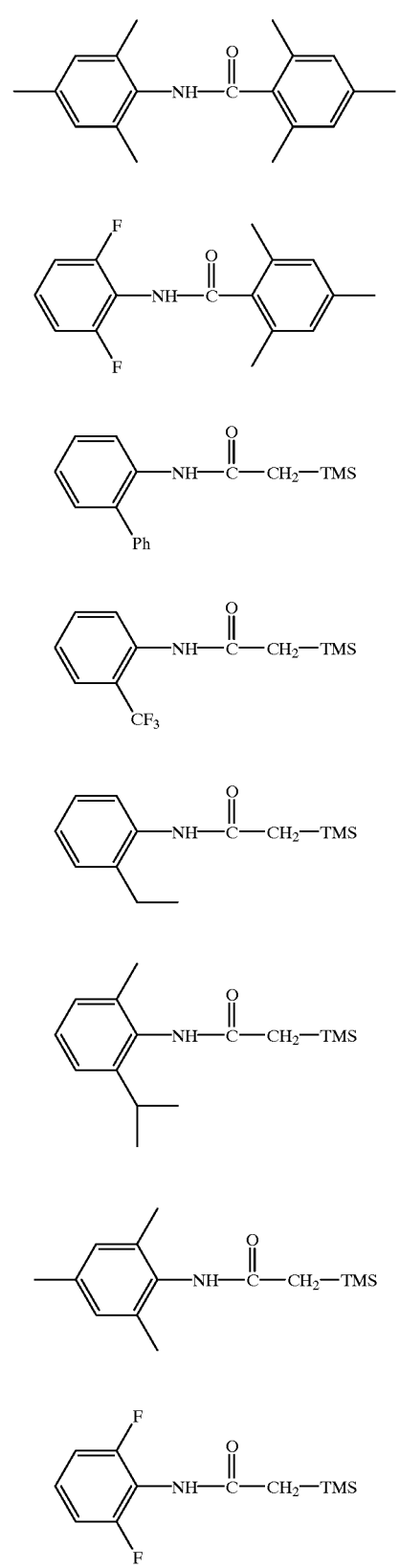

TABLE 5-continued
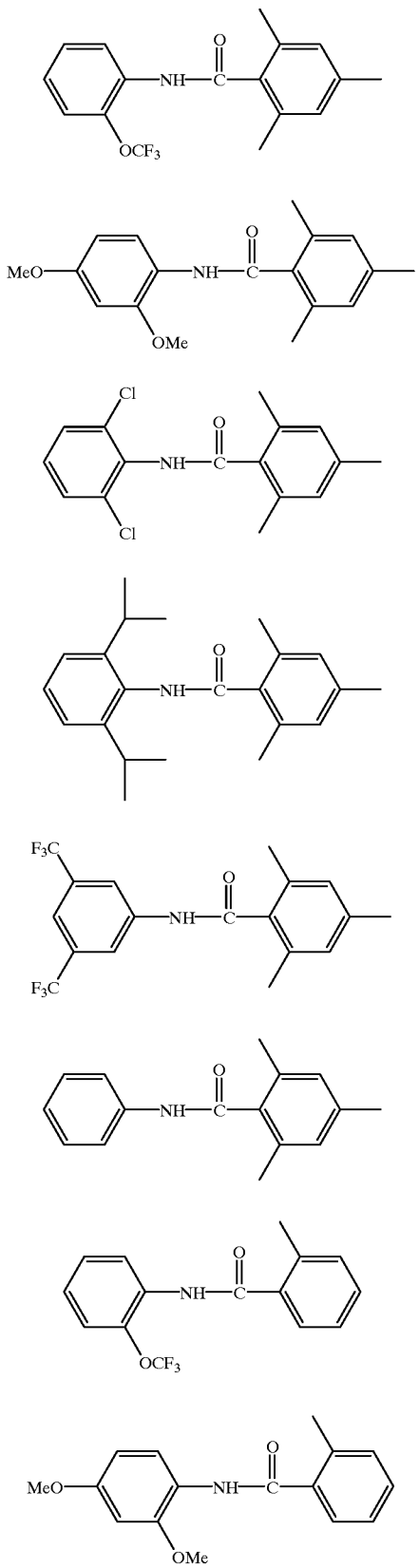
TABLE 5-continued
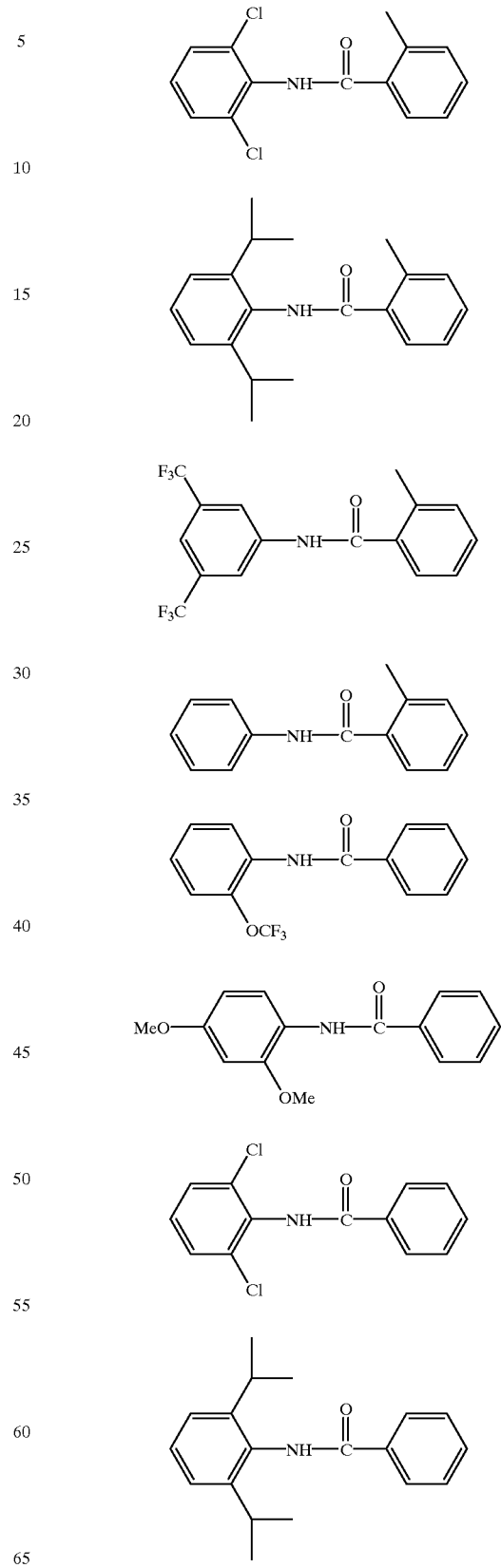

TABLE 5-continued
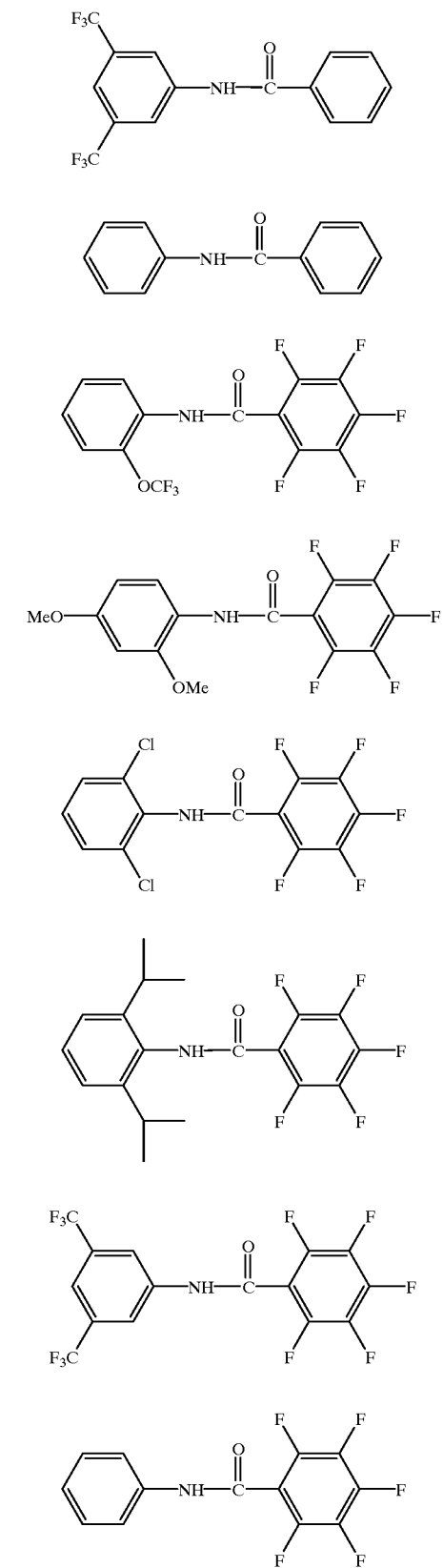
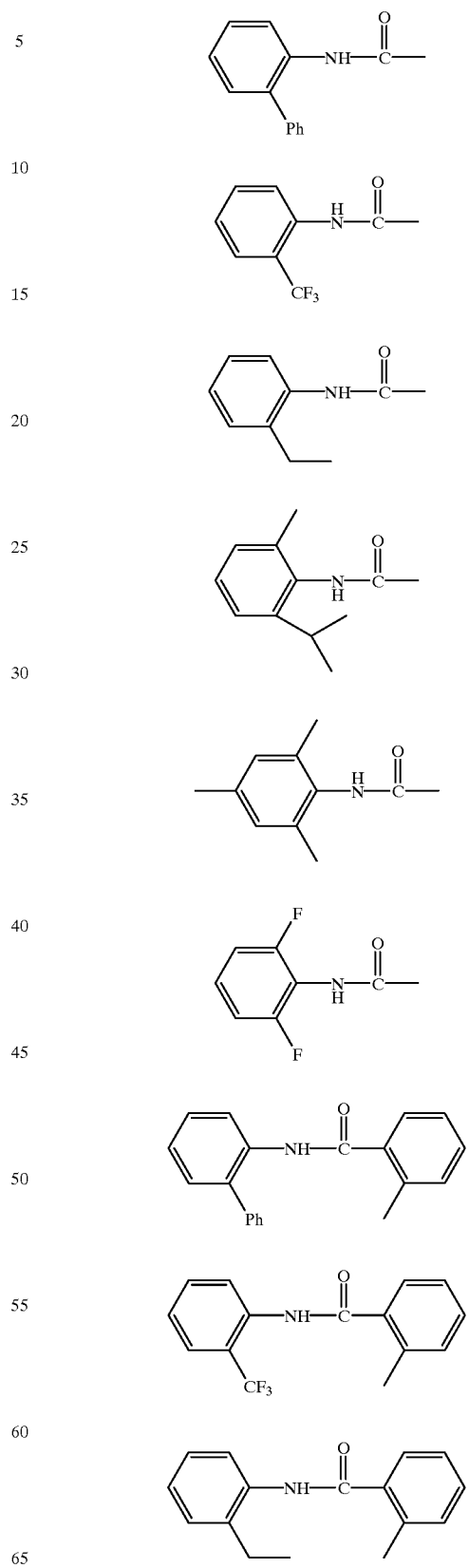

TABLE 5-continued
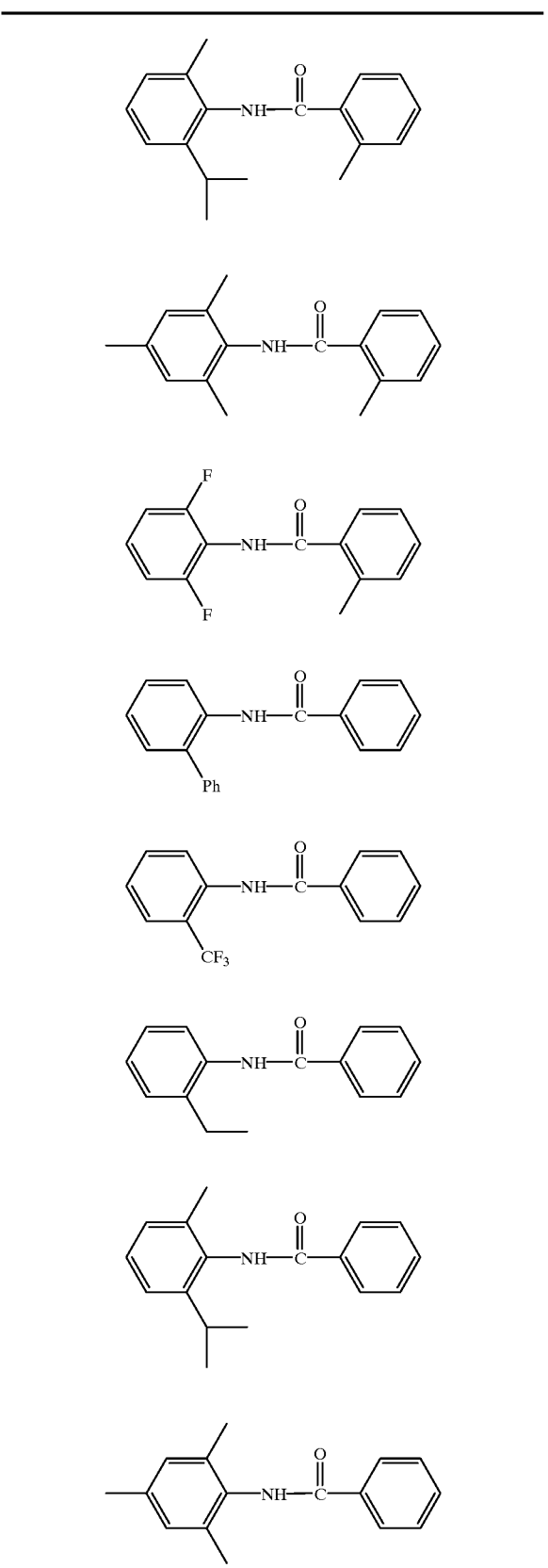
TABLE 5-continued
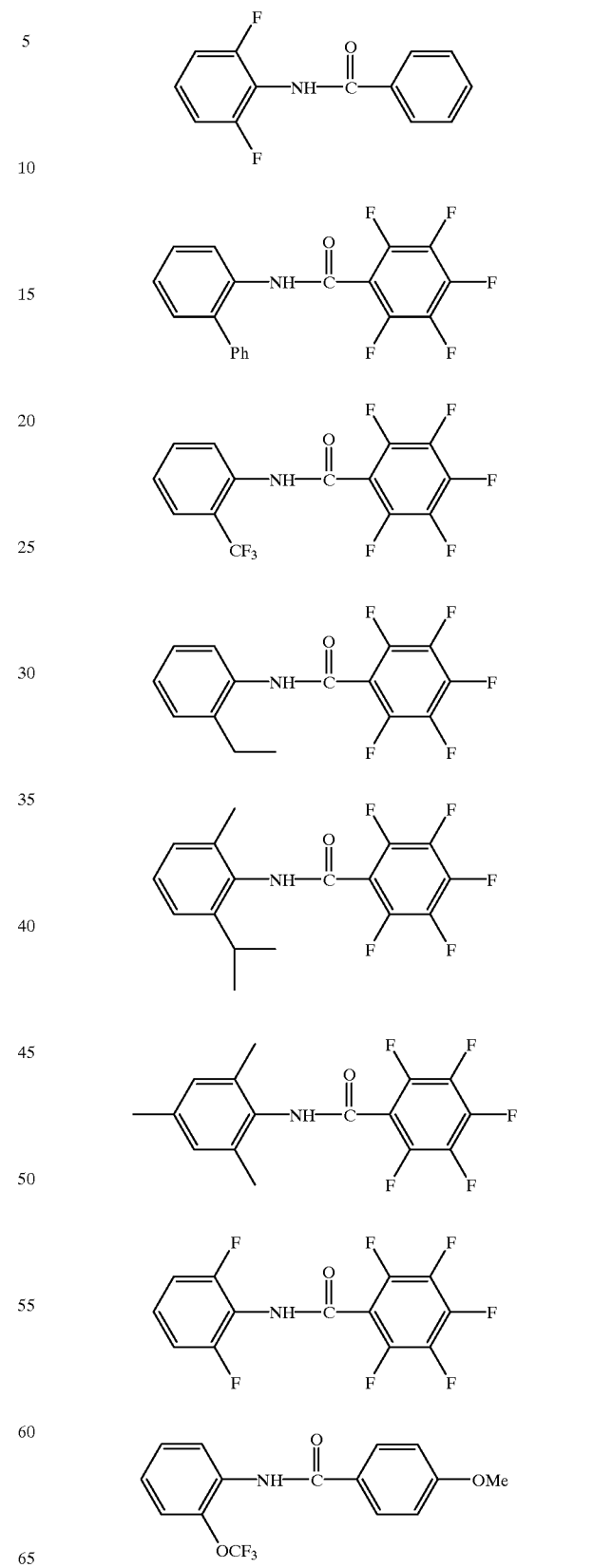

TABLE 5-continued
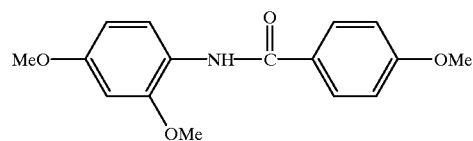
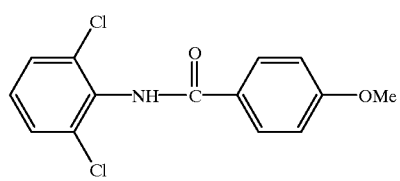
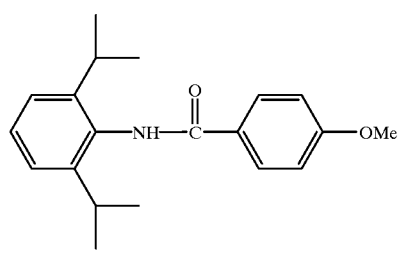
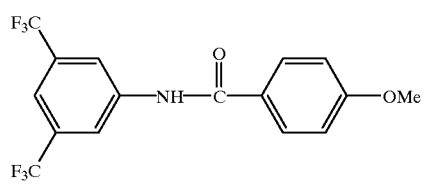
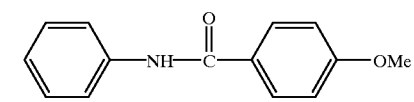
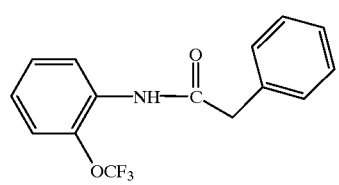
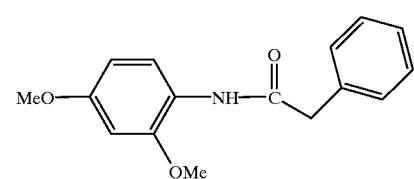
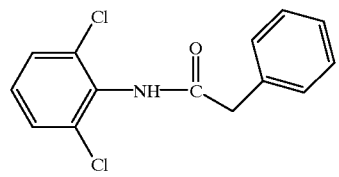
TABLE 5-continued
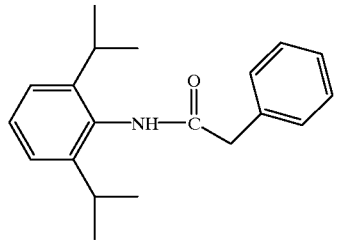
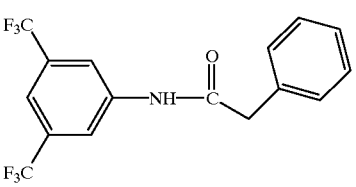
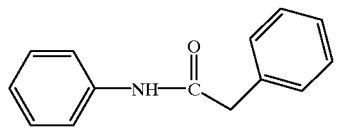
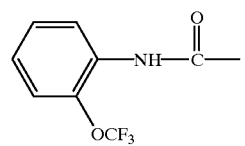
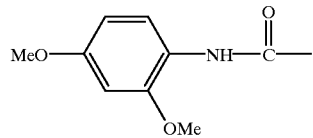
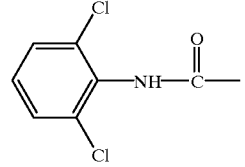
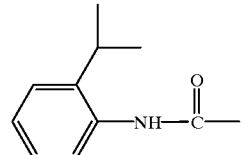
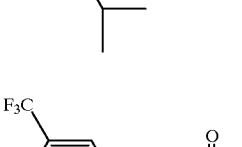
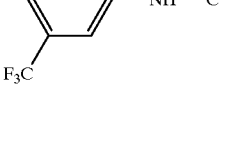

TABLE 5-continued
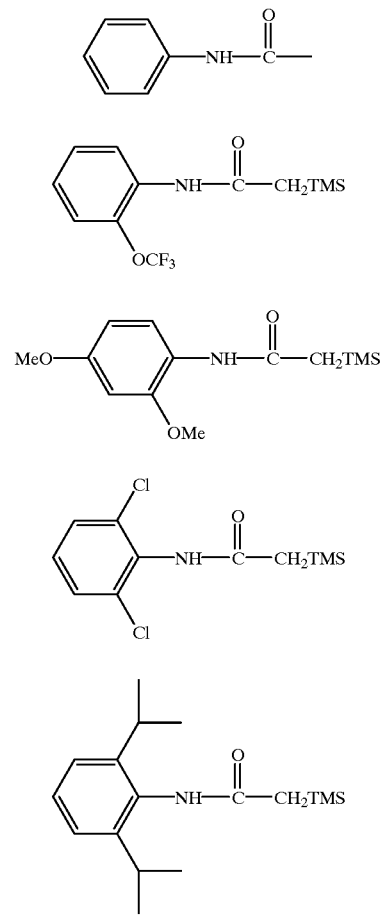
TABLE 5-continued
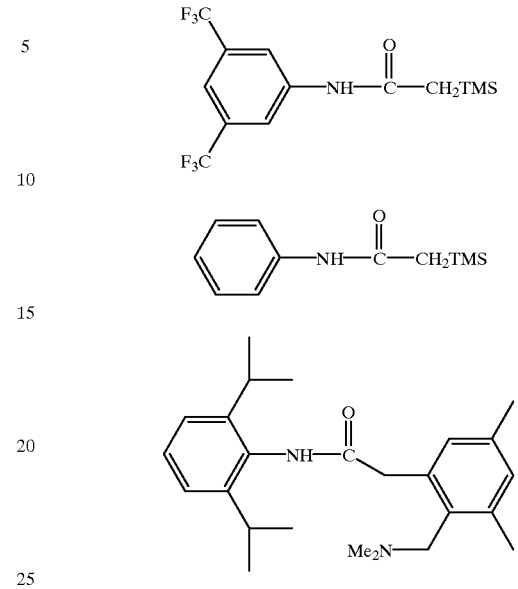
Another example of ancillary ligands of this invention include those ligands that can be represented by the formula:
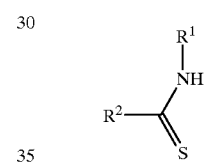
The nucleophiles listed Table I are combined with the isothiocyanates in Table 6, below, to prepare these ancillary ligands.
TABLE 6
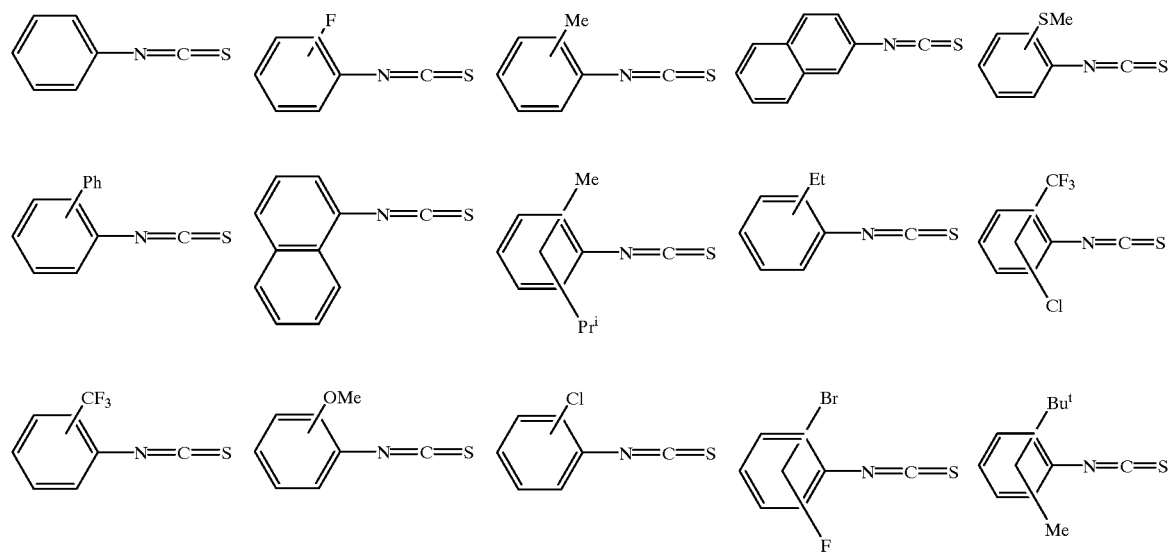

TABLE 6-continued
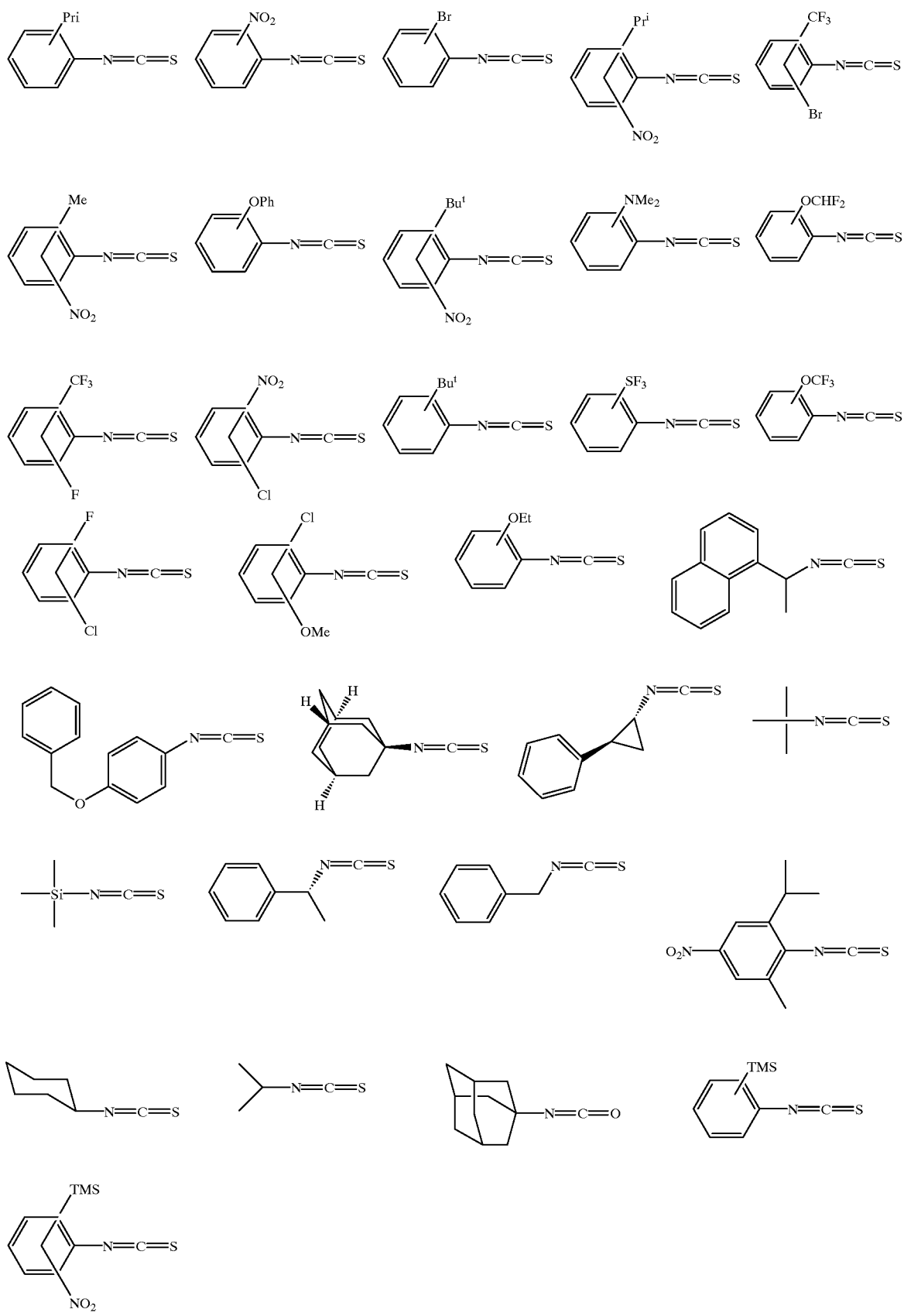

Another example of a class of ancillary ligands can be represented by the formula:

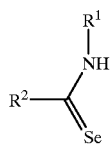

Isoselenocyanates can be prepared by treatment of isocyanides with elemental selenium in the presence of an appropriate base such as $Et_3N$. See for example Tetrahedron 1995, 41(21) 4781–4785. Isoselenocyanates can then be combined with the nucleophiles in Table 1 in a manner described in Scheme 1 to prepare the ligands of this class.

Once the ligand is formed, it is attached to the metal in a ligand exchange reaction, which may be represented by either of the following schemes:

Scheme 3

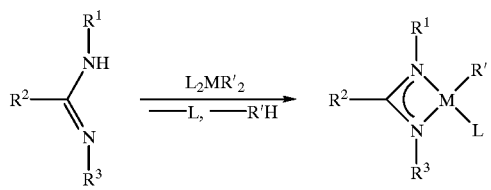

Scheme 4

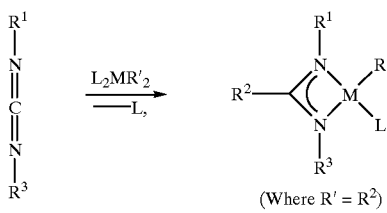

(Where R' = R²)

Scheme 5

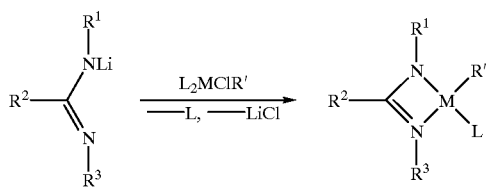

Scheme 6

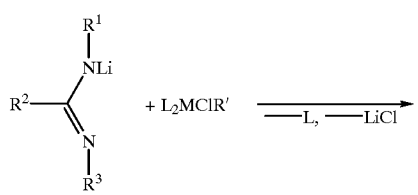

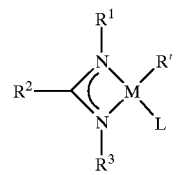

Scheme 7

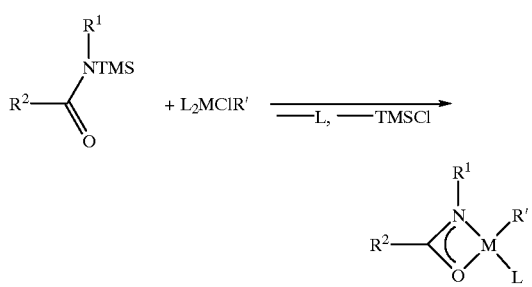

Scheme 8

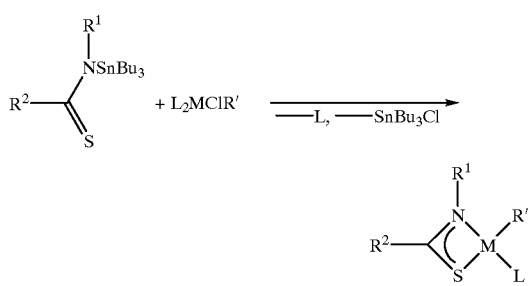

In Scheme 3, the metal precursor compound $L_2MR'_2$ loses one L ligand and one R' ligand, with the R' ligand gaining a hydrogen atom due to the reaction. L, M and R' are as defined above. In Scheme 4, the metal precursor compound $L_2MR'_2$ loses one L ligand and one R' ligand, but the R' ligand becomes attached to the central carbon atom on the ancillary ligand and becomes $R^2$ (which is shown in Scheme 2 by R'=R²). In Scheme 5, the metal precursor compound $L_2MClR'$, loses chlorine and one L ligand and the R' group remains attached. Schemes 6, 7 and 8 provide additional alternatives to compound synthesis. With either Scheme 3–8, the reaction is performed in a suitable non-interfering solvent (discussed below) and at a suitable temperature. In view of this specification, those of skill in the art can devise alternatives to these schemes without departing from the invention.

Suitable solvents for the synthesis of the compounds of this invention include aliphatic and aromatic hydrocarbons and halohydrocarbons, ethers, and cyclic ethers. Examples include straight and branched-chain hydrocarbons such as isobutane, butane, pentane, hexane, octane and mixtures thereof; cyclic and alicyclic hydrocarbons such as cyclohexane and methylcyclohexane and mixtures thereof; aromatic and hydrocarbon substituted aromatic compounds such as benzene, toluene and the like; ethers, such as tetrahydrofuran and diethylether, etc.

Recovery of the desired product from the reaction mixture can be by means known to those skilled in the art. The recovery process can include separation of by-products, if any, and evaporation of the solvent. The compounds may be worked up by extraction, recrystallization or other purification processes known to those skilled in the art. For example, an insoluble product or reactant can be removed by filtration or other separation technique.

In alternative embodiments, the metal compound is not recovered. In this case, the catalyst system is a composition of the ancillary ligand and the metal precursor. Thus, ancillary ligands can be described by the general formula:

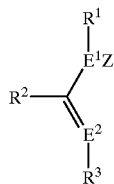

where $E^1$ and $E^2$ are elements, each of which is, independently, selected from the group consisting of N, P, O, S and Se;

Z is an element or molecule selected from the group consisting of H, Li, TMS, $SnBU_3$, Na, K, Rb, Ti, Ag and MgT, where T is a halogen (F, Cl, Br and I);

$R^1$ and $R^3$ are groups that may be independently selected from the group consisting of alkyl, substituted alkyl, aryl and substituted aryl;

$R^2$ is a group that may be selected from the group consisting of hydrocarbyl, alkoxides, aryloxides (—OX), thioethers, (—SX) phosphines (—$PX_2$), arsines (—$AsX_2$), silanes (—$SiX_3$), germanes (—$GeX_3$), amides (—NX2) and combinations thereof. In each of these formulas, X is selected from the group consisting of alkyls, aryls, substituted alkyls and substituted aryls and combinations thereof.

The ancillary ligand is combined with a metal precursor to form a composition. The metal precursors can be described by the general formula:

where M is a metal selected from Groups 2–12 of the Periodic Table of Elements. In other embodiments, M may be chosen from any of Groups 2, 3, 4, 5, 6, 7, 8, 9, 10, 11 or 12 of the Periodic Table of Elements.

R' is a group that forms a bond with M such that an olefin, diolefin or acetylenically unsaturated monomer or a functionalized version thereof (such as a functionalized olefin) can insert into the bond between R' and M. R' is typically selected from the group consisting of hydrocarbyl, silyl, germyl and hydride; a is 1, 2, 3 or 4 depending on the oxidation state of M.

L is an optional ligand, which, when present is a dative ligand (including agostic interactions), which can be selected from the group consisting of olefins, functionalized olefins, ethers, pyridines, nitriles, thioethers, phosphines, amines carbonyls and combinations thereof; and b is 0, 1, 2, 3 or 4.

T is a halogen and c is 0, 1 or 2. The number of halogens possible is dependant on the R' chosen, as those of skill in the art will appreciate.

The compositions and compounds of this invention are active catalysts either alone or in combination with an activator. When an activator or activating technique is used, those of skill in the art may use alumoxanes, strong Lewis acids, compatible noninterfering activators and combinations of the foregoing. The foregoing activators have been taught for use with different metal complexes in the following references, which are hereby incorporated by reference in their entirety: U.S. Pat. Nos. 5,599,761, 5,616,664, 5,453,410, 5,153,157, 5,064,802, and EP-A-277,003. Ratios of neutral complex to activator are on the order of 1 to 1000 to 1000 to 1. More specifically, a ratio of about 1 to 1 is preferred. A scavenger can also be used with this invention. Scavengers useful herein include metal complexes, alumoxanes, aluminum alkyls and the like.

The compositions, compounds and catalysts herein may be used to polymerize ethylenically or acetylenically unsaturated monomers having from 2 to 50 carbon atoms either alone or in combination. Monomers include $C_2$ to $C_{50}$ α-olefins such as ethylene, propylene, 1-butene, 1-hexene, 1-octene, 4-methyl-1-pentene, styrene and mixtures thereof. Monomers include functionalized monomers, such as those discussed in WO 96/23010, which is hereby incorporated by reference.

Because the compounds and catalysts of this invention usefully polymerize functionalized monomers, novel polymers copolymers or interpolymers may be formed. Specifically, functionalized monomers, when copolymerized with ethylene, form polymers having unique physical and melt flow properties. Such polymers can be employed alone or with other polymers in a blend to form products that may be molded, cast, extruded or spun. End uses for the polymers made with the catalysts of this invention include films for packaging, trash bags, foams, coatings, insulating devices and household items. Also, such functionalized polymers are useful as solid supports for organometallic or chemical synthesis processes.

Polymerization can be carried out in the Ziegler-Natta or Kaminsky-Sinn methodology, including temperatures of from −80° C. to 400° C. and pressures from atmospheric to 3000 atmospheres. Suspension, solution, slurry, gas phase or high-pressure polymerization processes may be employed with the catalysts and compounds of this invention. Such processes can be run in a batch or continuous mode. Examples of such processes are well known in the art. A support for the catalyst may be employed, which may be alumina, silica or a polymers support. Methods for the preparation of supported catalysts are known in the art. Slurry, suspension, solution and high-pressure processes use a suitable solvent as known to those skilled in the art.

EXAMPLES

The following examples are supplementary to the examples and illustrative ligands, compounds and compositions discussed above.

As necessary, experiments were carried out in an inert atmosphere using nitrogen or argon as the inert gas and following practices standard to those of skilled in the art for these types of reactions (for example, see Shriver, D. F. The Manipulation of Air-Sensitive Compounds, 2nd ed. (New York: Wiley, c1986)). Elemental analysis was performed by QTI Inc., Whitehouse, N.J. NMR spectra were taken on a Bruker Avance™ 300 MHz, using XWINNMR software. Except where noted, all starting compounds and solvents were obtained from J. T. Baker, Inc. or Aldrich and used without further purification. Dry solvents were obtained from Aldrich in Sure-Seal™ bottles and used without further purification. Deuterated solvents were purchased from Aldrich or Cambridge Isotopes, Inc. and used as is or dried according to standard procedures published in Perrin, D. D.; Armarego, W. L. F. *Purification of Laboratory Chemicals*, 3$^{rd}$ Ed.; Pergamon: New York, 1989.

SYNTHESIS EXAMPLES

EXAMPLE 1

Synthesis of N,N'-Substituted Benzamidines

To a solution of carbodiimide (1 mmol) in 10 mL of anhydrous $Et_2O$ under $N_2$ was added dropwise with stirring 667 mL (1.2 mmol) of 1.8 M PhLi in $Et_2O$/cyclohexane. After stirring for 2 h, 1 mL of 3 M HCl was added and the pH of the aq. layer was adjusted to 6 with aq. $NaHCO_3$. The org. layer was separated, dried over $Na_2SO_4$, and the volitiles were removed in vacuo. The resultant solid was dissolved in hexanes and loaded onto a 1×2 cm silica plug. After elution of a small amount of biphenyl, the eluent was changed to 1:1 hexanes/$Et_2O$ and the product was run off. Removal of the solvent in vacuo provided the substituted benzamidine as a white powder.

EXAMPLE 2

Synthesis of Bis(2,6diisopropylphenyl)carbodiimide

A mixture of 2.03 g (10 mmol) of 2,6-diisopropylphenylisocyanate and 10 mg (0.05 mmol) of 3-methyl-1-phenyl-3-phospholene-1-oxide were heated together at 100° C. under $N_2$ for 48 h. The resultant oil was vacuum sublimed to provide 1.43 g (79%) of bis(2,6-diisopropylphenyl)carbodiimide as a white powder.

EXAMPLE 3

Synthesis of Bis(2,6-diisopropylphenyl)benzamidine

To a solution of 363 mg (1 mmol) of of bis(2,6diisopropylphenyl)carbodiimide in 10 mL of anhydrous $Et_2O$ under $N_2$ was added dropwise with stirring 667 mL (1.2 mmol) of 1.8 M PhLi in $Et_2O$/cyclohexane. After stirring for 2 h, 1 mL of 3 M HCl was added and the pH of the aq. layer was adjusted to 6 with aq. $NaHCO_3$. The org. layer was separated, dried over $Na_2SO_4$, and the volitiles were removed in vacuo. The resultant solid was dissolved in hexanes and loaded onto a 1×2 cm silica plug. After elution of a small amount of biphenyl, the eluent was changed to 1:1 hexanes/$Et_2O$ and the product run off. Removal of the solvent in vacuo provided 1.03 g (85%) of bis(2,6-diisopropylphenyl)benzamidine $(C_6H_5)CN(C_6H_{3-2,6}-Pr^i_2)$ $NH(CH_3-2,6-Pr_2)$ as a white powder.

EXAMPLE 4

Prep of $\{(C_{65})CN(C_6H_5)_2\}Ni(CH_2SiMe_3)(NC_5H_5)$.

To a solution containing 3.5 mg $(C_6H_5)C(NC_6H_5)NH$ $(C_6H_5)$ in 1 mL deuterobenzene was added 5 mg of $(C_5H_5N)_2Ni(CH_2SiMe_3)_2$. The solution was stirred for minutes after which time the benzene was removed under vacuum producing 4 mg of $\{(C_6H_5)C(N(C_6H_5)_2)\}Ni$ $(CH_2SiMe_3)(NC_5H_5)$ (70%).

EXAMPLE 5

Prep of $\{(C_6H_5)CN(C_6H_3-2,6-Pr^i_2)_2)Ni(CH_2SiMe_3)$ $(NC_5H_5)$.

To a solution containing 0.1 g $(C_6H_5)CN(C_6H_{3-2,6}Pr^i_2)$ $NH(C_6H_3-2,6-Pr^i_2)$ in 10 mL toluene was added 0.09 g $(C_5H_5N)_2Ni(CH_2SiMe_3)_2$. The resultant mixture was a stirred overnight, filtered, and the solvent removed under a stream of argon to produce $\{(C_6H_5)CN(C6H_{3-2,6}-Pr^i_2)_2\}Ni$ $(CH_2SiMe_3)(NC_5H_5)$ as an orange oil (0.13 g, 85%).

EXAMPLE 6

Synthesis of $[((Pr^i)NC(DMAT)N(Pr^i))NiBr]$ 2 mmoles of diisopropylcarbodiimide were stirred in 10 mL of diethylether at room temperature. To this solution, 2 mmoles of (DMAT)Li were added over a period of 10 minutes. After the addition was complete, the resulting suspension was stirred for one hour during which time it turned into an almost clear solution. This solution was added to a bright yellow suspension of $(DME)NiBr_2$ in 5 mL of diethylether at room temperature. Immediately, the colour of the suspension turned brown/orange. The reaction mixture was stirred overnight, after which time it had turned into a greenish/greyish suspension. Filtration resulted in a greenish residue and purple solution. The filtrate was evaporated to dryness and extracted with 4 mL of dichloromethane. After filtration, the residue was concentrated and pentane was added. Crystallization afforded purple crystals of the title compound. Satisfying elemental analysis was obtained.

EXAMPLE 7

Synthesis of $[((Pr^i)NC(DMAT)N(PR^i))CoCl].OEt_2$

The synthesis was carried out in a similar way as described in example 6, except now 2 mmoles of $COCl_2$ were used instead of $(DME)NiBr_2$. After stirring overnight a suspension was obtained which was filtered. The blue solid residue was extensively washed with ether. The combined ether layers were evaporated to dryness and extacted with pentane. The pentane layers were evaporated to dryness yielding the title compound as a green oil.

EXAMPLE 8

Synthesis of $[((Pr)NC(DMAT)N(Pr^i)_2CrCl_2]$

The synthesis was performed in a similar way as described in example 6, except now on a mmole scale with $CrCl_3$. 3THF as the metal source. After stirring overnight, the suspension was filtered and the filtrate was concentrated. Crystallization afforded the title compound as a purple solid.

Polymerization Examples

Example A—$\{(C6HI_5)CN(C_6H_3-2,6-Pr^i_2)_2\}Ni(CH_2SiMe_3)$ $(NC_5H_5)$.

To a solution of 0.10 g of $(C_6H_5)CN(C_6H_3-2,6-Pr^1_2)_2\}Ni$ $(CH_2SiMe_3)(NC_5H_5)$ prepared as in Example 5 in 20 mL toluene was added 0.075 g $B(C_6F_5)_3$ in a thick walled glass reactor. After stirring for 10 minutes an overpressure of ethylene (20 psi) was applied for 2 hours during which time the mixture became warm. After 2 hours the ethylene pressure was released and the precipitated polyethylene was collected by filtration (0.3 g). The toluene was removed from the filtrate to afford an additional 0.2 g polyethylene.

Example B

Under inert atmosphere conditions, toluene solutions of the ancillary ligands (0.5 ml of 0.03 M solutions) shown in Table 7, below, were treated with the metal precursor $(C_5H_5N)_2Ni(CH_2SiMe_3)_2$ (0.25 ml of a 0.06 M toluene solution) over a period of 3 hours.

TABLE 7

| 1 | 2 | 3 |
|---|---|---|
| (structure) | (structure) | (structure) |

| 4 | 5 |
|---|---|

After this period the solutions were treated with $B(C_6F_5)_3$ (0.25 ml of a 0.18 M solution in toluene) and made up to 5 ml with toluene. The polymerization reactions were performed in a semi-batch polymerization reactor, with each vessel in the reactor having a volume of about 15 ml. Polymerizations were carried out under identical conditions of 25° C. at 50 psi of ethylene. Procedurally, the catalyst solution prepared as discussed above was added to each vessel under an inert atmosphere of $N_2$. Each vessel was closed and ethylene was introduced at a pressure of 50 psi. Ethylene was continuously fed to the reactor for a period of 1 hour at which time the reactions were stopped. Polyethylene was recovered from each polymerization reaction by evaporation of the solvent at 80° C., with the yield in mg presented in Table 8, below such that the rows and columns corresponding to Table 7 for identification of the ancillary ligand employed:

TABLE 8

|   | 1   | 2   | 3   | 4   | 5   |
|---|-----|-----|-----|-----|-----|
| A | 40  | 25  | 180 | 60  | 30  |
| B | 40  | 150 | 25  | 50  | 60  |
| C | 120 | 30  | 80  | 150 | 120 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the fill scope of equivalents to which such claims are entitled. The disclosures of all articles and reference, including patent application and publication, are incorporated herein by reference for all purposes.

What is claimed is:

1. A compound having the general formula:

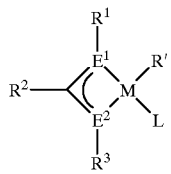

or a dimer or trimer or higher aggregate thereof,
wherein M is selected from the group consisting of Groups 7–12 of the Periodic Table of Elements;
$E^1$ and $E^2$ are, independently, selected from the group consisting of N, P, O, S and Se;
R' is selected from the group consisting of hydrocarbyl, silyl, germyl, hydride and combinations thereof;
L is optional, but when present is a dative ligand that shares electrons with M;
R' and $R^3$ are, independently, selected from the group consisting of alkyl, substituted alkyl, aryl, substituted aryl and combinations thereof;
$R^2$ is selected from the group consisting of alkyl, substituted alkyl, aryl, substituted aryl, acyl, hydride, alkoxy, phosphino, mercapto, saturated cyclic hydrocarbon, heteroaryl, substituted heteroaryl, heteroarylalkyl, substituted heteroarylalkyl, heterocycles, substituted heterocycles, heterocyclicalkyl, substituted heterocyclicalkyl, arsines, silanes, germanes, aminos, and combinations thereof, provided that when R' is hydrocarbyl, L is selected from the group consisting of acetylenes, olefins, functionalized olefins, ethers, pyridines, nitrites, thioethers, carbonyls, acteylenes, phosphines, amines and combinations thereof.

2. The compound of claim 1, wherein R' is selected from the group consisting of methyl ethyl, propel isopropyl, butyl t-butyl, i-butyl benzyl, phenyl, 2.46-trimethylphenyl cyclohexyl, butadieneyl pentadieneyl, trimethylsilyl, trimethylgermyl, triethylsilyl (trimethylsilyl)methyl, bis(triethylsilyl)methyl, tris(trimethylsilyl)methyl and pentafluorophenyl.

3. The compound of claim 1 wherein R' has less than 50 non-hydrogen atoms.

4. The compound of claim 1, wherein L is selected from the group consisting of olefins, functionalized olefins, ethers, pyridines, nitriles, thioethers, carbonyls, acteylenes, phosphines, amines and combinations thereof.

5. The compound of claim 1, where $R^2$ has less than 50 non-hydrogen atoms.

6. The compound of claim 5, wherein $R^2$ is selected from the group consisting of methyl, ethyl, propyl, butyl, t-butyl, pentyl, hexyl, phenyl, 2,4,6-trimethylphenyl, trimethylsilyl, perfluorophenyl, 2,6-diisopropylphenyl, hydride, neopentyl, trimethylsilylmethyl, p-methoxyphenyl, m- methoxyphenyl, p-chlorophenyl, fluorophenyl, ferrocenyl, benzyl, dibenzylamide, 2,4,6-$Me_3C_6H_2$-anilide, phenylacetylide, benzylamide, and crosslinked polystyrene.

7. The compound of claim 5, wherein $R^2$ further binds to M via a dative bond through an atom selected from the group consisting of N, S, P and O.

8. The compound of claim 7, wherein $R^2$ is selected from the group consisting of

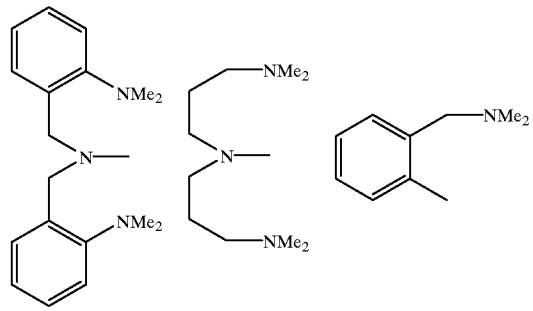

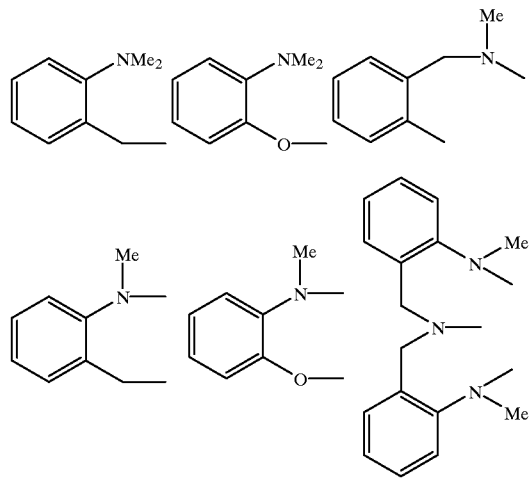

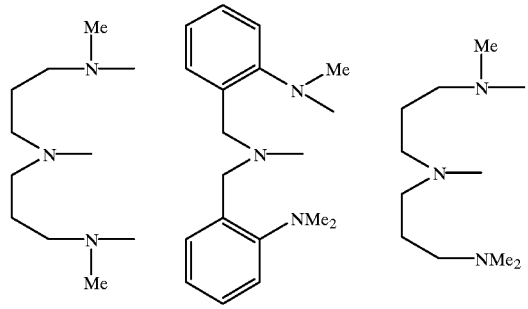

-continued

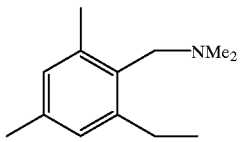

9. A compound having one of the following general formulas:

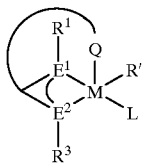 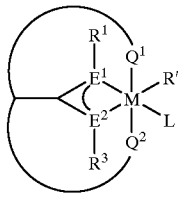

or a dimer or trimer or higher aggregate thereof,
wherein M is selected from the group consisting of Groups 4–12 of the Periodic Table of Elements;
$E^1$ and $E^2$ are, independently, selected from the group consisting of N, P, O, S and Se;
R' is a group that allows an olefin, diolefin, acetylenically unsaturated monomer or a functionalized version thereof to insert into the bond between R' and M;
L is optional, but when present is a dative ligand that shares electrons with M;
R' and $R^3$ are, independently, selected from the group consisting of alkyl, substituted alkyl, aryl, substituted aryl and combinations thereof;
Q, $Q^1$, and $Q^2$ independently, each occurrence, include an atom selected from the group consisting of N, O, S and P.

10. The compound of claim 9, wherein each of Q, $Q^1$ and $Q^2$ is independently selected from the group consisting of heteroarylalkyls, substituted heteroarylalkyls, heterocyclicalkyls, substituted heterocyclicalkyls, alkylamines and combinations thereof.

11. A compound having one of the following general formulas:

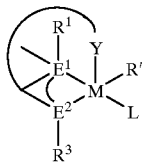 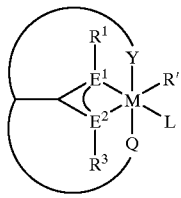

or a dimer or trimer or higher aggregate thereof,
wherein M is selected from the group consisting of Groups 3–10 of the Periodic Table of Elements;
$E^1$ and $E^2$ are, independently, selected from the group consisting of N, P, O, S and Se;
R' is a group that allows an olefin, diolefin, acetylenically unsaturated monomer or a functionalized version thereof to insert into the bond between R' and M;
L is optional, but when present is a dative ligand that shares electrons with M;
$R^1$ and $R^3$ are, independently, selected from the group consisting of alkyl, substituted alkyl, aryl, substituted aryl and combinations thereof;

Q and Y, independently, include an atom selected from the group consisting of N, O, S and P.

12. The compound of claim 11, wherein Y is selected from the group consisting of heteroarylalkyls, substituted heteroarylalkyls, heterocyclicalkyls, substituted heterocyclicalkyls, alkylamines and combinations thereof.

13. The compound of claim 12, wherein R' is selected from the group consisting of hydrocarbyl, silyl, germyl, hydride and combinations thereof.

14. The compound of claim 13, wherein R' has less than 50 non-hydrogen atoms.

15. A compound having the following general formula:

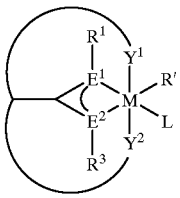

or a dimer or trimer or higher aggregate thereof,
wherein M is selected from the group consisting of Groups 4 of the Periodic Table of Elements;
$E^1$ and $E^2$ are, independently, selected from the group consisting of N, P, O, S and Se;
R' is a group that allows an olefin, diolefin, acetylenically unsaturated monomer or a functionalized version thereof to insert into the bond between R' and M;
L is optional, but when present is a dative ligand that shares electrons with M;
$R^1$ and $R^3$ are, independently, selected from the group consisting of alkyl, substituted alkyl, aryl, substituted aryl and combinations thereof;
$Y^1$ and $Y^2$, independently, include an atom selected from the group consisting of N, O, S and P.

16. The compound of claim 15 wherein $Y^1$ and $Y^2$ are independently selected from the group consisting of heteroarylalkyls, substituted heteroarylalkyls, heterocyclicalkyls, substituted heterocyclicalkyls, alkylamines and combinations thereof.

17. A process of polymerizing monomers, comprising the step of contacting a monomer with a compound having the general formula:

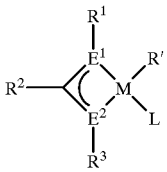

or a dimer, trimer or higher aggregate thereof
wherein M is selected from the group consisting of Groups 7–12 of the Periodic Table of Elements;
$E^1$ and $E^2$ are, independently, selected from the group consisting of N, P, O, S and Se;
R' is a group that allows an olefin, diolefin, acetylenically unsaturated monomer or a functionalized version thereof to insert into the bond between R' and M;
L is a dative ligand that shares electrons with M;
R' and $R^3$ are, independently, selected from the group consisting of alkyl, substituted alkyl, aryl, substituted aryl and combinations thereof;

$R^2$ is selected from the group consisting of alkyl, substituted alkyl, aryl, substituted aryl, acyl, hydride, alkoxy, phosphino, mercapto, saturated cyclic hydrocarbon, heteroaryl, substituted heteroaryl, heteroarylalkyl, substituted heteroarylalkyl, heterocycles, substituted heterocycles, heterocyclicalkyl, substituted heterocyclicalkyl, arsines, silanes, germanes, aminos, and combinations thereof.

18. The process of claim 17, wherein the compound is combined with an activator.

19. A composition comprising an ancillary ligand described by the general formula:

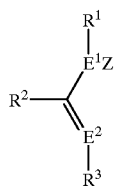

where $E^1$ and $E^2$ are elements, each of which is, independently, selected from the group consisting of N, P, O, S and Se;

Z is an element or molecule selected from the group consisting of H, L, TMS, $SnBu_3$, Na, K, Rb, Ti, Ag and MgT, where T is a halogen;

$R^1$ and $R^3$ are groups that may be independently selected from the group consisting of alkyl, substituted alkyl, aryl and substituted aryl;

$R^2$ is a group that may be selected from the group consisting of hydrocarbyl, alkoxides, aryloxides, thioethers, phosphines, arsines, silanes, germanes, amides and combinations thereof; and a metal precursor described by the general formula:

$R'_a ML_b T_c$ where M is a metal selected from Groups 2–12 of the Periodic Table of Elements;

R' is selected from the group consisting of hydrocarbyl, silyl, germyl and hydride; a is 1, 2, 3 or 4 depending on the oxidation state of M;

L is an optional ligand, which, when present is a dative ligand selected from the group consisting of olefins, functionalized olefins, ethers, pyridines, nitrites, thioethers, phosphines, amines carbonyls and combinations thereof; and b is 0, 1, 2, 3 or 4;

T is Cl, I, Br or F and c is 0, 1 or 2.

20. The composition of claim 1 wherein M is selected from the group consisting of Ni, Pd, Pt, Co, Fe, Mn and Zn.

21. The composition of claim 9 wherein M is selected from the group consisting of Ni, Pd, Pt, Co, Fe, Mn and Zn.

22. The compound of claim 2, wherein L is selected from the group consisting of acetylenes, olefins, functionalized olefins, ethers, pyridines, nitrites, thioethers, carbonyls, acteylenes, phosphines, amines and combinations thereof.

23. The compound of claim 2 wherein L is selected from the group consisting of ethylene, propylene, dimethylether, methylethylether, acetonitrile, benzonitrile, pentafluorobenzonitrile, p-trifluoromethylbenzonitrile, 3,5-bis(trifluoromethyl)benzonitrile, tetrahydrofuran, trimethylphosphine, triphenylphosphine, dimethylphenylamine, pyridine, lutidine, and 4-$Bu^1$-pyridine.

24. The compound of claim 23, wherein $R^2$ further binds to M via a dative bond through an atom selected from the group consisting of N, S, P and O.

* * * * *

UNITED STATES PATENT AND TRADEMARK OFFICE
CERTIFICATE OF CORRECTION

PATENT NO. : 6,242,623 B1
DATED : June 5, 2001
INVENTOR(S) : Boussie et al.

It is certified that error appears in the above-identified patent and that said Letters Patent is hereby corrected as shown below:

Column 93,
Line 44, "R'" should be replaced with -- $R^1$ --
Line 57, "nitrites" should be replaced with the word -- nitriles --
Line 60, a comma should be inserted after the word "methyl"
Line 60, the word "propel" should be replaced with the word -- propyl, --
Line 61, a comma should be inserted after the word "i-butyl"
Line 61, "2 46-trimethylphenyl" should be replaced with -- 2,4,6-trimethylphenyl, --
Line 64, "(triethylslyl)methyl," should be replaced with -- (trimethylsilyl)methyl, --

Column 94,
Line 12, "fluorophenyl," should be replaced with -- p-fluorophenyl --

Column 95,
Line 31, "R'" should be replaced with -- $R^1$ --
Line 50, the first formula should be replaced with:

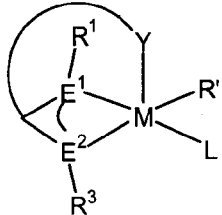

Column 96,
Line 25, "a -- -10 -- should be inserted after the number "4"

Column 97,
Line 27, "L," should be replaced with -- Li --
Line 27, "Ti" should be replaced with -- Tl --

UNITED STATES PATENT AND TRADEMARK OFFICE
CERTIFICATE OF CORRECTION

PATENT NO. : 6,242,623 B1
DATED : June 5, 2001
INVENTOR(S) : Boussie et al.

It is certified that error appears in the above-identified patent and that said Letters Patent is hereby corrected as shown below:

<u>Column 98,</u>
Line 11, the word "nitrites," should be replaced with -- nitriles, --
Line 21, the word "nitrites," should be replaced with -- nitriles, --
Line 29, "4-Bu$^1$-" should be replaced with -- 4-Bu$^t$- --

Signed and Sealed this

Twentieth Day of May, 2003

JAMES E. ROGAN
*Director of the United States Patent and Trademark Office*